US011000257B2

(12) United States Patent
Adler et al.

(10) Patent No.: US 11,000,257 B2
(45) Date of Patent: May 11, 2021

(54) DIGITAL STETHOSCOPES, AND AUSCULTATION AND IMAGING SYSTEMS

(71) Applicant: BAT CALL D. ADLER LTD., Nesher (IL)

(72) Inventors: Doron Adler, Haifa (IL); David Linhard, Haifa (IL); Inbal Avraham, Nesher (IL); Liat Adler, Haifa (IL); Liran Ziso Avraham, Nesher (IL)

(73) Assignee: SANOLLA LTD., Nesher (IL)

( * ) Notice: Subject to any disclaimer, the term of this patent is extended or adjusted under 35 U.S.C. 154(b) by 351 days.

(21) Appl. No.: 16/068,111

(22) PCT Filed: Feb. 15, 2017

(86) PCT No.: PCT/IB2017/050833
§ 371 (c)(1),
(2) Date: Jul. 4, 2018

(87) PCT Pub. No.: WO2017/141165
PCT Pub. Date: Aug. 24, 2017

(65) Prior Publication Data
US 2019/0000413 A1    Jan. 3, 2019

Related U.S. Application Data

(60) Provisional application No. 62/296,113, filed on Feb. 17, 2016.

(51) Int. Cl.
A61B 5/091    (2006.01)
A61B 7/04    (2006.01)
(Continued)

(52) U.S. Cl.
CPC ............... *A61B 7/04* (2013.01); *A61B 5/091* (2013.01); *A61B 5/6805* (2013.01); *A61B 7/003* (2013.01);
(Continued)

(58) Field of Classification Search
CPC ......... A61B 7/04; A61B 5/091; A61B 5/6805; A61B 7/003; A61B 8/08; A61B 8/4209;
(Continued)

(56) References Cited

U.S. PATENT DOCUMENTS 3,433,959 A    3/1969 Atwood et al.
3,580,082 A    5/1971 Strack et al.
(Continued)

FOREIGN PATENT DOCUMENTS

CN    103479385 A    1/2014
CN    103479386 A    1/2014
(Continued)

OTHER PUBLICATIONS

Kirgizov., U.S. Appl. No. 29/630,202, filed Dec. 20, 2017.
(Continued)

*Primary Examiner* — Navin Natnithithadha
(74) *Attorney, Agent, or Firm* — Kligler & Associates Patent Attorneys Ltd

(57) ABSTRACT

Described embodiments include a system (74), including a garment (76), configured to cover at least a portion of a body of a subject, one or more sound transmitters (92) coupled to the garment, configured to transmit sound (128) through the body of the subject, and a plurality of sound detectors (22, 96) coupled to the garment. The sound detectors are configured to detect the transmitted sound following passage of the transmitted sound through the body of the subject, to detect body sound (25) emanating from the body of the subject, and to generate a plurality of sound-detector outputs in response to detecting the transmitted sound and the body sound. The system further includes a processor (98), configured to process the sound-detector outputs, and to generate a processor output in response thereto. Other embodiments are also described.

21 Claims, 8 Drawing Sheets

(51) Int. Cl.
| | |
|---|---|
| *A61B 8/08* | (2006.01) |
| *H04R 1/46* | (2006.01) |
| *H04R 17/02* | (2006.01) |
| *A61B 5/00* | (2006.01) |
| *H04R 1/40* | (2006.01) |
| *H04R 3/00* | (2006.01) |
| *H04R 23/00* | (2006.01) |
| *A61B 7/00* | (2006.01) |
| *A61B 8/00* | (2006.01) |

(52) U.S. Cl.
CPC .............. *A61B 8/08* (2013.01); *A61B 8/4209* (2013.01); *A61B 8/5207* (2013.01); *H04R 1/406* (2013.01); *H04R 1/46* (2013.01); *H04R 3/005* (2013.01); *H04R 17/02* (2013.01); *H04R 23/008* (2013.01); *A61B 5/0044* (2013.01); *A61B 5/6804* (2013.01); *H04R 2201/023* (2013.01); *H04R 2201/401* (2013.01); *H04R 2430/20* (2013.01)

(58) Field of Classification Search
CPC ... A61B 8/5207; A61B 5/0044; A61B 5/6804; A61B 5/87; A61B 8/5215; H04R 1/406; H04R 1/46; H04R 3/005; H04R 17/02; H04R 23/008; H04R 2201/023; H04R 2201/401; H04R 2430/20
USPC .................................. 600/529, 534, 538, 586
See application file for complete search history.

(56) References Cited

U.S. PATENT DOCUMENTS

| | | | |
|---|---|---|---|
| 4,792,145 | A | 12/1988 | Eisenberg et al. |
| 5,853,005 | A | 12/1998 | Scanlon |
| 6,154,551 | A | 11/2000 | Frenkel |
| 6,520,924 | B2 | 2/2003 | Lee |
| 6,699,204 | B1 | 3/2004 | Kehyayan et al. |
| 6,778,673 | B1* | 8/2004 | Hobelsberger ......... G10K 11/02 381/96 |
| 6,788,417 | B1 | 9/2004 | Zumberge et al. |
| 7,458,939 | B2 | 12/2008 | Munk |
| 7,976,480 | B2 | 7/2011 | Grajales et al. |
| 3,015,878 | A1 | 9/2011 | Melikechi et al. |
| 8,419,652 | B2 | 4/2013 | Rajamani et al. |
| 8,475,396 | B2 | 7/2013 | Jones et al. |
| 8,920,343 | B2 | 12/2014 | Sabatino |
| 9,101,274 | B2 | 8/2015 | Bakema et al. |
| 9,277,330 | B2 | 3/2016 | Aharoni et al. |
| 9,445,779 | B2 | 9/2016 | Shams et al. |
| 10,842,416 | B2* | 11/2020 | Joseph ................... A61B 5/022 |
| 10,881,330 | B2* | 1/2021 | Joseph ................. A61B 5/0006 |
| 2001/0030077 | A1 | 10/2001 | Watson |
| 2002/0071570 | A1 | 6/2002 | Cohen et al. |
| 2002/0183642 | A1 | 12/2002 | Murphy |
| 2004/0260193 | A1 | 12/2004 | LaSala |
| 2005/0222515 | A1 | 10/2005 | Polyshchuk et al. |
| 2005/0273015 | A1* | 12/2005 | Bauer ..................... A61B 7/04 600/528 |
| 2006/0070623 | A1 | 4/2006 | Wilkinson et al. |
| 2007/0050715 | A1 | 3/2007 | Behar |
| 2008/0013747 | A1 | 1/2008 | Tran |
| 2009/0316925 | A1 | 12/2009 | Eisenfeld et al. |
| 2011/0137209 | A1 | 6/2011 | Lahiji et al. |
| 2011/0222697 | A1 | 9/2011 | Dong et al. |
| 2011/0224988 | A1 | 9/2011 | Mahajan et al. |
| 2013/0041278 | A1 | 2/2013 | Bai et al. |
| 2014/0073864 | A1 | 3/2014 | Engelbrecht et al. |
| 2014/0155762 | A1 | 6/2014 | Maskara et al. |
| 2014/0290372 | A1 | 10/2014 | Lagaros et al. |
| 2015/0073306 | A1 | 3/2015 | Abeyratne et al. |
| 2015/0119758 | A1 | 4/2015 | Rogers et al. |

FOREIGN PATENT DOCUMENTS

| | | |
|---|---|---|
| CN | 203506748 U | 4/2014 |
| CN | 107510473 A | 12/2017 |
| DE | 202005006661 U1 | 8/2005 |
| KR | 20120040530 A | 4/2012 |
| WO | 9325874 A1 | 12/1993 |
| WO | 2002009586 A2 | 2/2002 |
| WO | 2006075263 A1 | 7/2006 |
| WO | 2011117862 A2 | 9/2011 |
| WO | 2014163443 A1 | 10/2014 |
| WO | 2017141165 A1 | 8/2017 |

OTHER PUBLICATIONS

Padmanabhan et al., "Accelerometer type cardiac transducer for detection of low-level heart sounds", IEEE Transactions on Biomedical Engineering, vol. 40, No. 1, pp. 21-28, Jan. 1, 1993.
International Application # PCT/IB2017/050833 search report dated Jul. 3, 2017.
Adler et al., U.S. Appl. No. 15/953,502, filed Apr. 16, 2018.
Bukhman et al., "Spectral analysis of acoustic vibrations on the surface of the human body," Acoustical Physics, vol. 41, Issue 1, 10 pages, 1995.
International Application # PCT/IB2018/056335 search report dated Dec. 26, 2018.
International Application # PCT/IB2018/056336 search report dated Dec. 25, 2018.
European Application # 17752765.2 search report dated Oct. 8, 2019.
European Application # 20168052.7 Search Report dated Jun. 29, 2020.
U.S. Appl. No. 15/953,502 Office Action dated Sep. 11, 2020.
U.S. Appl. No. 15/953,502 Office Action dated Feb. 19, 2021.

* cited by examiner

DIGITAL STETHOSCOPES, AND AUSCULTATION AND IMAGING SYSTEMS

CROSS-REFERENCE TO RELATED APPLICATIONS

The present application claims priority from U.S. Provisional Appl. No. 62/296,113, filed Feb. 17, 2016, whose disclosure is incorporated herein by reference.

FIELD OF THE INVENTION

The present invention relates generally to the field of medical devices, and specifically to devices for the auscultation of sounds that emanate from the body, such as sounds that emanate from the heart or lungs, and the processing and playback of such sounds.

BACKGROUND

US Patent Application Publication 2011/0222697, whose disclosure is incorporated herein by reference, describes a method and system for locating a sound source. The system comprises a receiving unit for receiving navigating sound signals from at least two navigating sound sensors, and receiving a selection instruction comprising a signal segment type corresponding to the sound source, wherein the at least two navigating sound sensors are received in a chestpiece. The system further comprises a selecting unit for selecting a segment from each navigating sound signal according to the signal segment type, a calculating unit for calculating a difference between the segments selected from the navigating sound signal, and a generating unit for generating a moving indication signal for guiding moving the chest-piece to the sound source according to the difference.

U.S. Pat. No. 8,475,396, whose disclosure is incorporated herein by reference, describes a system and method for visualizing auditory scene analysis by way of a portable device. In one embodiment, the method steps include capturing multiple sounds from a sensor array of microphones connected to the portable device, performing auditory scene analysis on detected body sounds in accordance with a psychoacoustic representation of body organ functions, and rendering to a display of the portable device a visualization of auditory scene auscultation of the body sounds, including user input functionality for separated sound source tracks, sound source identifier tracks, and sound source location trajectories.

U.S. Pat. No. 6,154,551, whose disclosure is incorporated herein by reference, describes a microphone having linear optical transducers. The linear optical transducers are used in several configurations to detect the motion of one or more conventional microphone diaphragms in proportional response to incident acoustic signals. A light source, such as a laser or a light emitting diode directs light onto a reflecting microphone diaphragm responsive to sound waves, and the position of the reflected light is monitored using a position sensitive detector which effectively eliminates effects of light source intensity on the optical transducer-processed signal. Other embodiments make use of either a fixed knife edge or a knife edge which moves in response to the motion of the diaphragm to interrupt the light source in a proportional manner to the amplitude of motion of the diaphragm.

SUMMARY OF THE INVENTION

There is provided, in accordance with some embodiments of the present invention, a system that includes a garment, configured to cover at least a portion of a body of a subject, one or more sound transmitters coupled to the garment, configured to transmit sound through the body of the subject, and a plurality of sound detectors coupled to the garment. The sound detectors are configured to detect the transmitted sound following passage of the transmitted sound through the body of the subject, to detect body sound emanating from the body of the subject, and to generate a plurality of sound-detector outputs in response to detecting the transmitted sound and the body sound. The system further includes a processor, configured to process the sound-detector outputs, and to generate a processor output in response thereto.

In some embodiments,
the garment includes:
a back portion, configured to cover a back of the subject; and
one or more bands extending from the back portion, configured to cover a chest of the subject, and
the sound transmitters are coupled to the bands, and at least some of the sound detectors are coupled to the back portion.

In some embodiments, at least some of the sound detectors are arranged in a two-dimensional array.

In some embodiments, the sound transmitters are configured to transmit the sound at a first range of frequencies, and the sound detectors include:
a plurality of transmitted-sound detectors, configured to detect the transmitted sound by virtue of being configured to detect the first range of frequencies; and
a plurality of body-sound detectors, configured to detect the body sound by virtue of being configured to detect a second range of frequencies that is different from the first range of frequencies.

In some embodiments, the first range of frequencies is between 25 kHz and 200 kHz.

In some embodiments, the first range of frequencies is between 500 Hz and 10 kHz.

In some embodiments, the second range of frequencies includes infrasonic frequencies.

In some embodiments, each of at least some of the body-sound detectors is disposed together with a respective one of the sound transmitters, within a common housing.

In some embodiments, at least some of the body-sound detectors are interspersed among the transmitted-sound detectors.

In some embodiments,
the sound detectors include at least one line of three or more sound detectors, configured to output respective sound-detector outputs in response to detecting the body sound, and
the processor is configured, by processing the sound-detector outputs, to identify an angle, with respect to the line of sound detectors, of a source of the body sound.

In some embodiments, the sound detectors include at least three pairwise non-parallel lines, each having three or more sound detectors, and the processor is configured to identify a location of the source of the body sound, by identifying the angle of the source of the body sound with respect to each of the three lines.

In some embodiments, the sound detectors are arranged such that each of at least some of the sound detectors belongs to at least three of the lines.

In some embodiments, the processor is configured to identify the angle of the source of the body sound with respect to the line of sound detectors, by:
for each angle of a plurality of angles:

for each detector of the body-sound detectors, delaying the sound-detector output of the detector in accordance with the angle and with a position of the detector on the line, and summing the delayed sound-detector outputs, such as to yield a summed output, and identifying the angle of the source of the body sound as the angle for which a power of the summed output is highest, relative to others of the angles.

In some embodiments, the processor is configured to identify a location of a source of the body sound by applying a three-dimensional model, of at least a portion of the body of the subject, that includes a plurality of cells, and that indicates, for each cell of the cells, a time required for a sound wave emanating from the cell to reach each one of the sound detectors, when the subject is wearing the garment.

In some embodiments, the processor is configured to construct, by processing the sound-detector outputs, an image of an interior of the body of the subject, and the processor output includes the image.

In some embodiments, the processor is further configured to identify, by processing the sound-detector outputs, a location of a source of the body sound, and to indicate the location in the image.

In some embodiments, the sound transmitters are configured to transmit the sound through lungs of the subject.

In some embodiments, the processor is configured to estimate a volume of air in the lungs, responsively to respective delays with which the transmitted sound is detected by the sound detectors.

There is further provided, in accordance with some embodiments of the present invention, a method that includes, using one or more sound transmitters coupled to a garment that is worn by a subject, transmitting sound through a body of the subject. The method further includes, using a plurality of sound detectors coupled to the garment, detecting the transmitted sound following passage of the transmitted sound through the body of the subject, detecting body sound emanating from the body of the subject, and generating a plurality of sound-detector outputs in response to detecting the transmitted sound and the body sound. The method further includes, using a processor, processing the sound-detector outputs, and generating a processor output in response thereto.

There is further provided, in accordance with some embodiments of the present invention, apparatus for detecting sound waves emanating from a body of a subject, the apparatus including a housing and a membrane, disposed at an opening of the housing. The membrane is configured to deflect, when an outer face of the membrane contacts the body, responsively to the sound waves impinging on the membrane. The apparatus further includes a piezoelectric microphone, disposed within the housing, configured to detect vibrations of air caused by the deflection of the membrane, and to generate a microphone output in response thereto, an accelerometer, disposed on an inner face of the membrane, configured to deflect, along with the membrane, at frequencies below a minimum frequency that is detectable by the piezoelectric microphone, and to generate an accelerometer output in response thereto, and a processor, configured to process the microphone output and the accelerometer output, and to generate, responsively to the processing, a sound signal that represents the impinging sound waves.

In some embodiments, the membrane includes a material having a specific acoustic impedance that is between 0.8 and 4.5 MPa·s/m.

In some embodiments, the material is selected from the group consisting of: polyethylene, polyamide, and polymethyl methacrylate.

In some embodiments, the apparatus further includes a second microphone, disposed within the housing, configured to detect ambient noise that does not emanate from the body of the subject, and to generate a noise-detection output in response thereto, the processor being configured to generate the sound signal by adaptively filtering the microphone output, based on the noise-detection output.

In some embodiments, the apparatus further includes a printed circuit board (PCB) disposed within the housing, the piezoelectric microphone is mounted on a face of the PCB that faces the membrane, and the second microphone is mounted on an opposite face of the PCB, facing away from the membrane.

In some embodiments, the apparatus further includes a printed circuit board (PCB) disposed within the housing, and the processor and the microphone are mounted on the PCB.

In some embodiments, the apparatus further includes a display coupled to the housing such that the display faces away from the membrane, and the processor is further configured to analyze the sound signal, and to drive the display to display results of the analysis.

In some embodiments, the apparatus further includes earphones connected to the housing, and the processor is further configured to play the sound signal through the earphones.

In some embodiments, the processor is configured to play infrasonic components of the sound signal, which represent infrasonic components of the sound waves, by translating the infrasonic components of the sound signal to a range of audible frequencies.

In some embodiments, the processor is configured to translate the infrasonic components to the range of audible frequencies by:

computing a short-time Fourier transform (STFT) of the sound signal, decimating the STFT of the sound signal, in a time domain of the STFT of the sound signal, by a factor R, computing an inverse STFT of the decimated STFT of the sound signal, and interpolating the inverse STFT by the factor R.

In some embodiments, the range of audible frequencies is between 500 Hz and 4 kHz.

In some embodiments, the apparatus further includes a sound transmitter disposed within the housing, configured to transmit sound through the body of the subject.

In some embodiments, the sound transmitter is configured to transmit the sound at a frequency between 25 kHz and 200 kHz.

In some embodiments, the sound transmitter is configured to transmit the sound at a frequency between 500 Hz and 10 kHz.

In some embodiments, the sound transmitter is configured to transmit the sound by transmitting a chirp signal.

There is further provided, in accordance with some embodiments of the present invention, a method for detecting sound waves emanating from a body of a subject. The method includes, by contacting the body of the subject with an outer face of a membrane that is disposed at an opening of a housing, causing the membrane to deflect responsively to the sound waves impinging on the membrane. The method further includes, using a piezoelectric microphone disposed within the housing, detecting vibrations of air caused by the deflection of the membrane, and generating a microphone output in response thereto. The method further includes, using an accelerometer that is disposed on an inner face of the membrane, detecting the deflection of the membrane at frequencies below a minimum frequency that is detectable by the piezoelectric microphone, and generating an accelerometer output in response thereto. The method further includes, using a processor, processing the microphone output and the accelerometer output, and generating, responsively to the processing, a sound signal that represents the impinging sound waves.

In some embodiments, the sound waves emanate from lungs of the subject.

There is further provided, in accordance with some embodiments of the present invention, apparatus for detecting sound waves emanating from a body of a subject. The apparatus includes a housing, and a membrane, including an inner face at least part of which is optically reflective, disposed at an opening of the housing, configured to deflect, when an outer face of the membrane contacts the body, responsively to the sound waves impinging on the membrane. The apparatus further includes an array of photodetectors disposed within the housing, a light source, disposed within the housing, configured to transmit a beam of light onto the membrane, such that the beam of light is reflected by the inner face of the membrane onto the array of photodetectors at a location that varies as a function of the deflection of the membrane, and a processor, configured to identify the location at which the beam of light was reflected onto the array of photodetectors, and to output, responsively thereto, a sound signal that represents the impinging sound waves.

In some embodiments, the apparatus further includes earphones connected to the housing, and the processor is further configured to play the sound signal through the earphones.

In some embodiments, the membrane is mounted to an inside of the housing such that a perimeter of the membrane does not deflect responsively to the impinging sound waves.

In some embodiments, the array of photodetectors consists of fewer than 10 photodetectors.

In some embodiments, the processor is configured to identify the location at which the beam of light was reflected onto the array of photodetectors with a resolution that is less than a length of each of the photodetectors.

In some embodiments, the processor is configured to identify the location at which the beam of light was reflected onto the array of photodetectors by receiving, from each photodetector of the photodetectors, a signal having a magnitude that indicates an amount of light, from the reflected beam of light, that was detected by the photodetector, fitting the respective signal magnitudes to a Gaussian distribution, and identifying the location as a center of the Gaussian distribution.

In some embodiments, the apparatus further includes a cylindrical lens, configured to focus the beam of light into a line, such that the line is reflected onto the array of photodetectors.

In some embodiments, the apparatus further includes an accelerometer, coupled to the housing, configured to generate an accelerometer output in response to movements of a chest of the subject, when the outer face of the membrane contacts the chest of the subject.

In some embodiments, the processor is configured to identify the location at which the beam of light was reflected onto the array of photodetectors by continuously polling the photodetectors.

In some embodiments, a perimeter of the membrane is circular.

In some embodiments, the membrane has a convex shape.

In some embodiments, the membrane includes a horizontal perimeter portion mounted to an inside of the housing, a horizontal central portion, at a center of the membrane, and a slanted portion that joins the perimeter portion to the central portion.

There is further provided, in accordance with some embodiments of the present invention, a method for detecting sound waves emanating from a body of a subject. The method includes, by contacting the body of the subject with an outer face of a membrane that is disposed at an opening of a housing, at least part of an inner face of the membrane being optically reflective, causing the membrane to deflect responsively to the sound waves impinging on the membrane. The method further includes, using a light source disposed within the housing, transmitting a beam of light onto the membrane, such that the beam of light is reflected by the inner face of the membrane onto an array of photodetectors at a location that varies as a function of the deflection of the membrane, and, using a processor, identifying the location at which the beam of light was reflected onto the array of photodetectors, and outputting, responsively thereto, a sound signal that represents the impinging sound waves.

In some embodiments, the sound waves emanate from lungs of the subject.

The present invention will be more fully understood from the following detailed description of embodiments thereof, taken together with the drawings, in which:

DETAILED DESCRIPTION OF EMBODIMENTS

Overview

Figure 1:
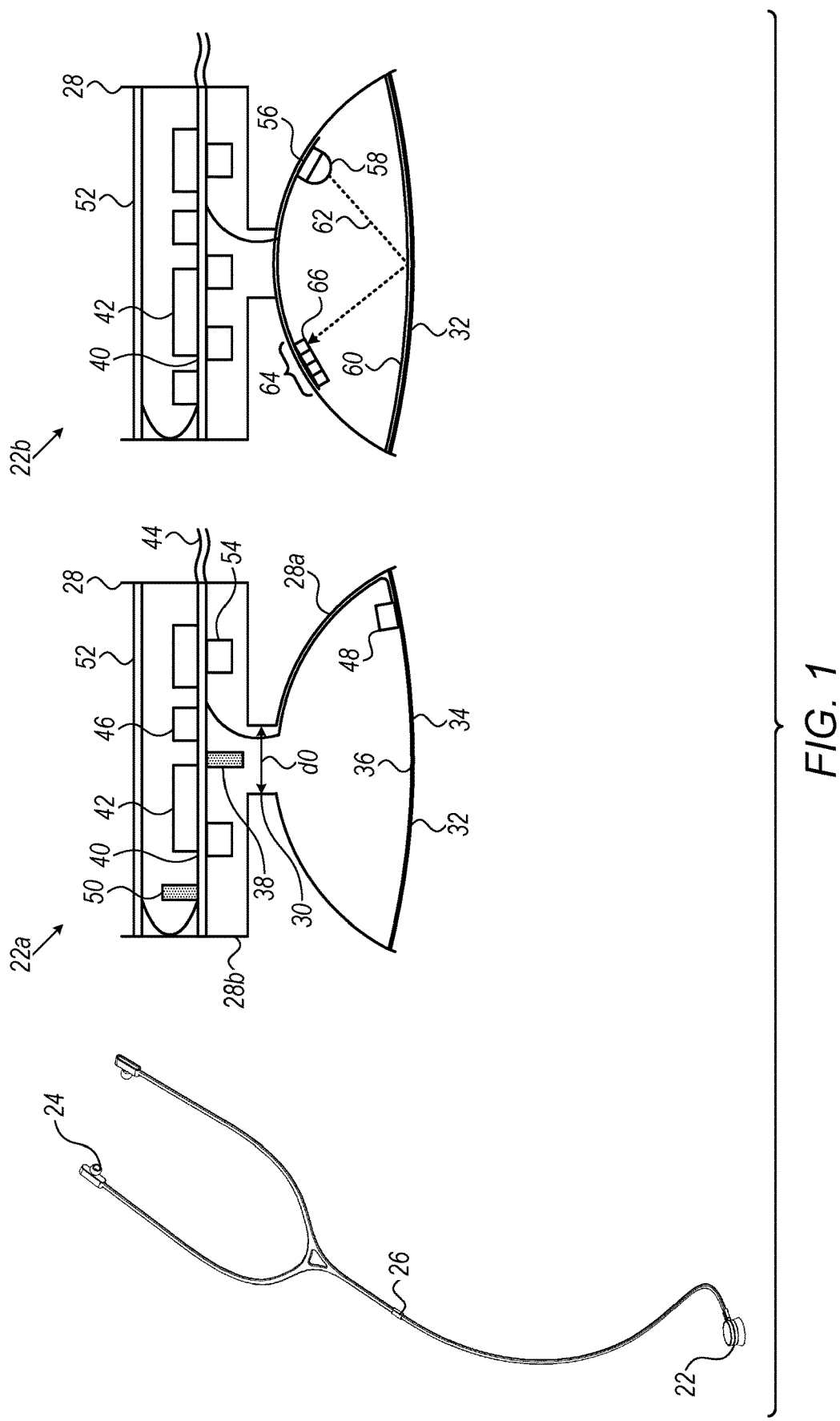
FIG. 1 is a schematic illustration of a digital stethoscope for detecting sonic and infrasonic sound waves emanating from a body of a subject, in accordance with some embodiments of the present invention.

Conventional stethoscopes allow a user to hear only those sounds that are within the hearing range of the human ear, which is generally between 20 and 20,000 Hz. However, several academic papers—such as Bukhman et al., "Spectral analysis of acoustic vibrations on the surface of the human body," Acoustical Physics 41.1 (1995): 41-48, which is incorporated herein by reference—have shown that sounds beneath the hearing range, referred to herein as infrasonic sounds, are also produced by the human body. Such infrasonic sounds may provide valuable information for facilitating a diagnosis. (In the context of the present specification, including the claims, "sonic sounds" (or "sonic sound waves") refer to sounds (or sound waves) having a frequency greater than 20 Hz, while "infrasonic sounds" (or "infrasonic sound waves") refer to sounds (or sound waves) having a frequency less than 20 Hz.)

Embodiments of the present invention therefore provide a digital stethoscope that allows the capture of both sonic and infrasonic sounds emanating from a human body, such as from the lungs of a human body. The stethoscope comprises a membrane, such as a circular membrane, which is typically fastened, at its edges, to a frame. As the membrane contacts the body, sound waves from the body—including both sonic and infrasonic sound waves—impinge on the membrane, causing deflections of the membrane. These deflections are then converted into digital signals that represent the original sound waves, including the infrasonic components of these sound waves. These signals may then be played to a user, analyzed by a processor (e.g., such as to automatically perform a diagnosis), and/or stored for later analysis. In some embodiments, the conversion of the membrane deflections into digital signals is performed by an optical system. In such embodiments, the stethoscope comprises a light source, such as a laser diode, which transmits a beam of light onto the membrane. The stethoscope further comprises an optical sensor, comprising an array of photodetectors. As the membrane deflects responsively to the impinging sound waves, the membrane reflects the light beam onto the optical sensor, at a location of incidence that varies in accordance with the amplitude of the impinging sound waves. Hence, by analyzing the variation in this location of incidence, a processor may reconstruct the sound waves.

Typically, the deflections of the membrane are relatively small, and hence, the position at which the reflected light beam strikes the optical sensor varies by only a small amount. Thus, the number of photodetectors in the optical sensor may be kept relatively small; for example, in some embodiments, the optical sensor comprises between two and five photodetectors. An advantage of a small number of photodetectors is that polling of these photodetectors may be done relatively quickly, facilitating a higher rate of sampling of the impinging sound waves, and hence, a better digital reconstruction.

Embodiments of the present invention further provide a technique for identifying the location of incidence with a resolution that is less than the length of a single photodetector. Per this technique, the reflected light beam is assumed to strike the optical sensor with a Gaussian distribution, and the center of this distribution is assumed to be the location of incidence of the reflected light beam.

In other embodiments, the conversion of the membrane deflections is performed by a piezoelectric microphone, configured to detect both sonic and infrasonic vibrations of air, alternatively to the optical system described above. In such embodiments, the impingement of sounds waves on the membrane causes the air within the stethoscope to vibrate, and these vibrations are then detected by the piezoelectric microphone. In some embodiments, an accelerometer is placed on the inner side of the membrane. This accelerometer may detect deflections of the membrane at infrasonic frequencies below the minimum frequency detectable by the piezoelectric microphone, thus allowing the detection of body sounds even at very low frequencies.

In some embodiments, the membrane is acoustically matched to the body, in that the membrane is made of a material having a specific acoustic impedance that is close to the specific acoustic impedance of the body, which is approximately equal to that of water, i.e., 1.48 MPa·s/m. Hence, provided that the membrane contacts the subject's body with little or no air in between, there is relatively little reflection of impinging sound waves, such that the sounds from the body may be more accurately detected. For example, the membrane may be made of polyethylene, which has a specific acoustic impedance of 2.2 MPa·s/m, polyamide (2.8 MPa·s/m), or polymethyl methacrylate (3.2 MPa·s/m).

Embodiments of the present invention further include a garment, comprising a plurality of sound detectors, such as a plurality of the above-described optical sound detectors, and/or a plurality of the above-described piezoelectric sound detectors. The garment is worn by a subject, such that the sound detectors are in contact with the subject's torso. Subsequently, upon a sound wave from the subject's body impinging on the sound detectors, a processor may identify the location of the source of the sound wave, based on the different times at which the detectors detected the sound wave. Knowing the location of the sound source may allow the physician to more easily perform a diagnosis.

For example, the detectors may be arranged in three or more linear arrays. Upon the detectors detecting a sound wave, the processor may, for each of the linear arrays, estimate the angle, with respect to the array, from which the sound wave emanated. Based on these angles, the processor may identify the location of the sound source.

Alternatively, the processor may locate the source of a sound wave using a model that, given the times at which the sound wave was detected by each of the detectors, returns the location of the sound-wave source. For example, the processor may construct (or at least utilize) a three dimensional grid that models the subject's torso, and may further compute, for each cell in this grid, the time required for a sound wave emanating from the cell to reach each of the sound detectors, assuming the sound detectors are positioned relative to the grid in accordance with their arrangement on the garment. Subsequently, given the respective detection times for a sound wave, the processor may apply this model in locating the source of the sound wave.

In some embodiments, the garment comprises one or more sound transmitters, configured to transmit sonic or ultrasonic sound signals through the subject's body, such as through the subject's lungs. Such transmitters may be contained, for example, within the housing of the above-described optical- or piezoelectric-based sound detectors, behind the respective membranes of these units. In such embodiments, the garment further comprises at least one array of sound detectors, positioned opposite the transmitters. Since each of the transmitted sound signals is received by a given detector with an intensity that is a function of the properties of the media lying between the transmitter of the signal and the detector, the processor may construct an image of the interior of the subject's body, based on the respective intensities with which the signals are received by the detectors. Such an image may be marked to show the location of the source of a particular body sound, identified, for example, as described above. If the sound signals are transmitted through the subject's lungs, the sound signals will be received by the detectors with a delay that is a function of the amount of air, within the lungs, through which the sound signals passed. Hence, the processor may further compute the amount of air in the lungs, based on the respective delays with which the signals were received.

In some embodiments, the array of sound detectors is also used for body-sound detection. In such embodiments, the garment need not necessarily comprise the optical- or piezoelectric-based body-sound detectors described above.

Typically, the garment comprises one or more accelerometers, configured to detect movements of the subject's chest (which typically have a frequency of 0.1-0.2 Hz). Such accelerometers may be disposed, for example, on or within the sound detectors described above, such as on the inner faces of the membranes of these detectors. Based on the detected chest movements, the processor may identify the various stages in the respiratory cycle of the subject, and may subsequently correlate this information with any measured lung volumes, acquired as described above, and/or using a spirometer.

Typically, the above-described processor, which locates body-sound sources, constructs images, calculates lung volumes, and/or performs any other functions described herein, is disposed remotely from garment, within a separate analysis unit that is wiredly or wirelessly connected to the garment. The analysis unit typically further comprises a user interface (UI), comprising, for example, a display, one or more speakers, and/or any suitable input devices. The UI may be used to provide relevant feedback to the user. For example, images, and/or any diagnoses automatically performed by the processor, may be displayed to the user on the display. Alternatively or additionally, digital body-sound signals from the sound detectors may be played to the user, via the speakers. To play infrasonic signals such that they are audible to the user, the processor may use a particular "frequency stretching" technique described herein, which translates the signals to higher frequencies while preserving the harmonic relationships of the signal. In some embodiments, for example, the infrasonic signals are translated to an audible range of frequencies near 1 kHz, such as 500 Hz-4 kHz.

Digital Stethoscope

Reference is initially made to FIG. 1, which is a schematic illustration of a digital stethoscope 20 for detecting sonic and infrasonic sound waves emanating from a body of a subject, in accordance with some embodiments of the present invention. Stethoscope 20 comprises a sound-detection unit 22 and two earphones 24. As described in detail below, sound-detection unit 22 is configured to detect sound emanating from the body of the subject, and to play the detected sound to a user, via earphones 24.

FIG. 1 shows respective cross-sections for two example embodiments of sound-detection unit 22: a piezoelectric-based sound-detection unit 22a, referred to hereinbelow as a "piezoelectric detector," and an optics-based sound-detection unit 22b, referred to hereinbelow as an "optical detector." Each of piezoelectric detector 22a and optical detector 22b comprises a housing 28, which houses the various detector components described below. In some embodiments, especially in the case of piezoelectric detector 22a, housing 28 comprises two separate compartments, connected to one another via a narrow neck 30 having an inner diameter d0 that is less than 15 mm. In particular, housing 28 may comprise a lower compartment 28a, which may be dome-shaped as shown in FIG. 1, and an upper compartment 28b, which may be, for example, disc-shaped.

Each of piezoelectric detector 22a and optical detector 22b further comprises a membrane 32, disposed at the lower opening of housing 28. To listen to sounds from the subject's body, a physician holds the membrane against the subject's body. Sound waves from the body then impinge on the membrane, causing the membrane to deflect. The deflection of the membrane is then translated into a sound signal, as described in detail below, and the sound signal is then played to the physician.

Figure 2:
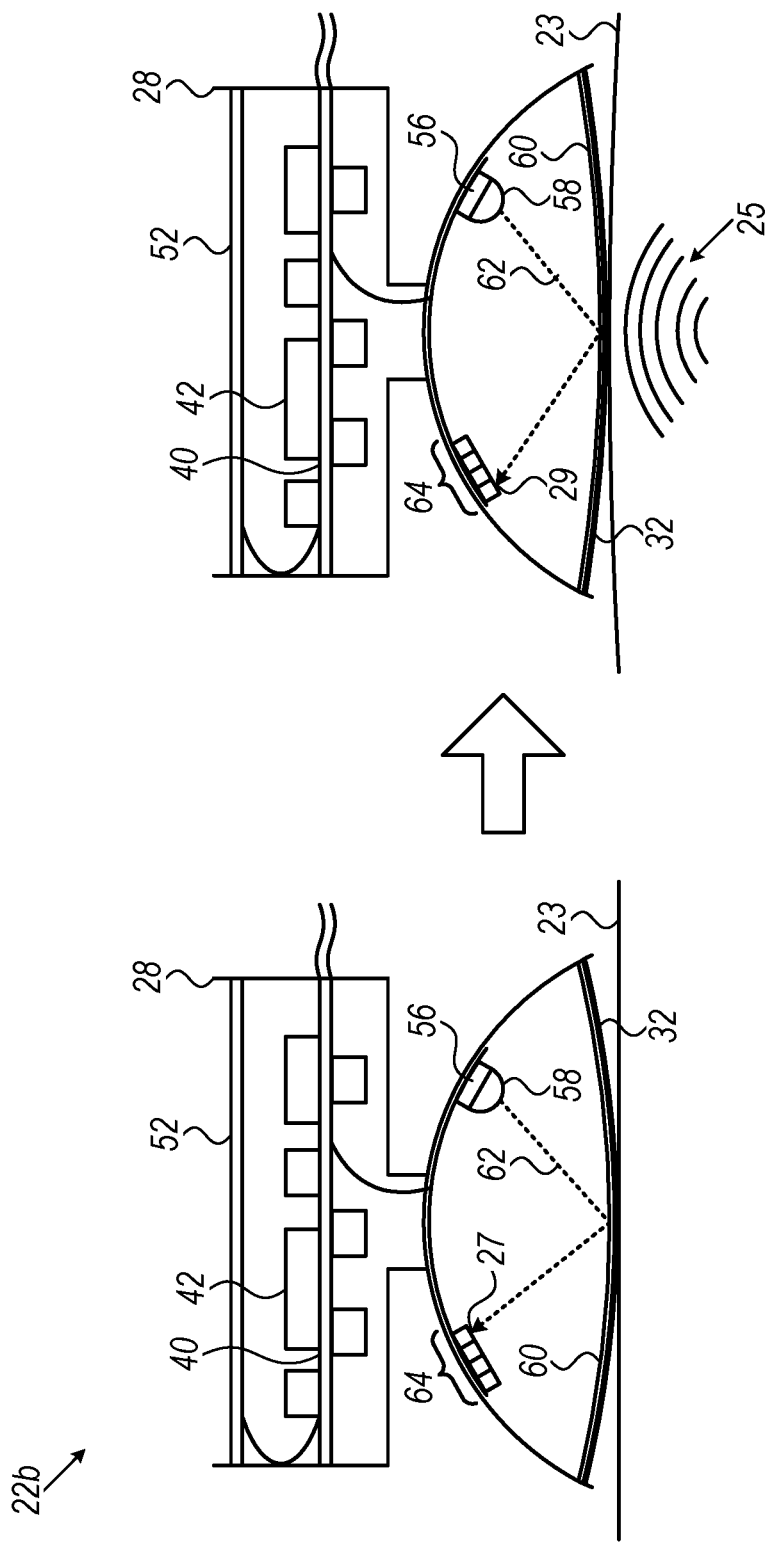
FIGS. 2-3 are schematic illustrations of the manner in which an optical detector operates, in accordance with some embodiments of the present invention.

In general, the perimeter of membrane 32 may have any suitable shape. For example, in embodiments in which lower compartment 28a is dome-shaped, such that the lower opening of lower compartment 28a is circular, the perimeter of membrane 32 may also be circular. Alternatively, for example, membrane 32 have an elliptical perimeter. In some embodiments, as shown in FIG. 1, membrane 32 has a convex shape, in that the membrane is curved outward from the housing. (In such embodiments, the membrane may retain its convex shape even when the membrane is held against the subject's body, as illustrated in FIG. 2.) Alternatively, the membrane may have any other suitable shape, such as the alternative shape shown in FIG. 3. Typically, the membrane is mounted to the inside of the housing such that the perimeter of the membrane does not deflect responsively to the impinging sound waves; rather, the perimeter of the membrane is held in place by the housing, and only a more central portion of the membrane deflects.

Membrane 32 may comprise any suitable material. For example, the membrane may comprise a material having a specific acoustic impedance that is between 0.8 and 4.5 MPa·s/m, such that the membrane is acoustically matched to the subject's body, as described above in the Overview. Examples of such materials include polyethylene, polyamide, and polymethyl methacrylate.

Typically, stethoscope 20 further comprises a power source 26, such as a battery, configured to power the various electronic components described below.

Pieozoelectric Detector

Piezoelectric detector 22a comprises a piezoelectric microphone 38, which may be mounted, for example, on a printed circuit board (PCB) 40 disposed within the housing, e.g., within upper compartment 28b. Typically, microphone 38 is mounted on the face of the PCB that faces membrane 32, such that, as the deflection the membrane causes the air within housing 28 (e.g., the air within lower compartment 28a) to vibrate, the microphone detects the vibrations, and generates a microphone output in response to the vibrations. (In other words, the microphone converts these vibrations to electrical signals.) In some embodiments, microphone 38 is placed at the upper end of neck 30, such that the air vibrations are amplified by neck 30, prior to reaching the microphone.

The microphone output is received by a processor 42, which may also be mounted on PCB 40. Processor 42 processes the microphone output, and generates, responsively to the processing, a sound signal that represents the impinging sound waves. The processor may then store the sound signal in a digital memory 46, which may also be mounted on PCB 40. Alternatively or additionally, the processor may analyze the sound signal, e.g., such as to perform an automatic diagnosis. Alternatively or additionally, the processor may play the sound signal through earphones 24, which may be connected to the housing via wires 44.

Typically, piezoelectric detector 22a further comprises an accelerometer 48, disposed on an inner face 36 of the membrane, which is opposite from the outer face 34 of the membrane that contacts the subject's body. Accelerometer 48 may serve at least two functions. First, when the detector contacts the chest of the subject, movement of the chest, caused by respiration of the subject, causes the detector to move, such that the accelerometer, by virtue of being coupled to the detector, detects these chest movements. Second, as sound waves impinge on the membrane, the accelerometer deflects along with the membrane, by virtue of being coupled to the membrane. The accelerometer may thus detect deflections of the membrane, including those deflections that are at frequencies below the minimum frequency that is detectable by the piezoelectric microphone. The accelerometer and piezoelectric microphone thus complement one another, in that the accelerometer detects sound at very low frequencies that are not detectable by the microphone, and the microphone detects sound at higher frequencies that are not detectable by the accelerometer.

In response to detecting movements of the chest and/or the deflections of the membrane, the accelerometer generates an accelerometer output, which is received and processed by processor 42. In processing the accelerometer output, the processor typically applies appropriate frequency filters to this output, such as to differentiate chest movements (which typically have a frequency of 0.1-0.2 Hz) from membrane deflections having higher or lower frequencies. The processor may then generate the sound signal, using both the membrane-deflection portion of the accelerometer output, and the output from piezoelectric microphone 38. The processor may also analyze the chest-movement portion of the accelerometer output, such as to identify the various stages in the respiratory cycle of the subject.

In some embodiments, the piezoelectric detector further comprises a second microphone 50, such as a second piezoelectric microphone, disposed within the housing, configured to detect ambient noise that does not emanate from the body of the subject. Typically, second microphone 50 is mounted on the opposite face of PCB 40 from the face on which piezoelectric microphone 38 is mounted. The second microphone thus faces outward, away from membrane 32 (and away from the subject), such as to facilitate the detection of ambient noise. In response to detecting ambient noise, the second microphone generates a noise-detection output, which is received by processor 42. In generating the sound signal, the processor adaptively filters the output from piezoelectric microphone 38, based on the noise-detection output from the second microphone. In other words, the processor uses the noise-detection output to guide the filtering of noise from the output received from piezoelectric microphone 38.

In other embodiments, the piezoelectric detector does not comprise second microphone 50. Instead, the processor uses sophisticated filtering techniques, such as time-varying filtering or adaptive filtering, to remove noise from the microphone output.

Typically, the detector further comprises a display 52, such as a liquid crystal display (LCD), coupled to housing 28 such that display 52 faces away from the membrane. For example, as illustrated in FIG. 1, display 52 may be mounted at the opening of upper compartment 28b. In some embodiments, processor 42 is configured to analyze the sound signal, and to drive display 52 to display the results of the analysis. For example, the processor may drive the display to display a diagnosis that was automatically performed, by the processor, based on the sound signal. Alternatively or additionally, the display may provide feedback to the physician. For example, the display may display a warning that the acquired sound signal is of poor quality, due the membrane being pressed against the subject with insufficient force. Alternatively or additionally, the display may comprise a touch screen, configured to receive touch-input from the physician. Such input may, for example, instruct the processor to perform a different type of analysis, guide the processor in performing an automatic diagnosis, or instruct the processor to display output in a different format.

Display 52 may have any suitable shape. For example, if upper compartment 28b is disc-shaped, display 52 may have a circular shape. In some embodiments, display 52 is adjustably mounted on housing 28; for example, the display may be mounted to a pivotable arm that is in turn mounted on the housing. In such embodiments, the angle and position of the display may be adjusted, such as to better allow the physician to see the display.

Typically, the detector further comprises one or more other electronic (hardware) components 54, which may also be mounted on PCB 40. For example, the detector may comprise electronic components for filtering, buffering, and amplifying any output received from the microphones, and/ or analog-to-digital (A/D) converters for converting any analog outputs from the microphones and/or accelerometer to a digital form that is readable by the processor. Alternatively or additionally, the detector may comprise a digital-to-analog (D/A) converter for converting the digital sound signal, which is output by the processor, into an analog form that is playable to the user via earphones 24, and/or electronic components for filtering and amplifying the analog signal before this signal reaches the earphones. Alternatively or additionally, the detector may comprise a power-supply manager, configured to manage and/or monitor the supply of power from power source 26. For example, the power-supply manager may cause display 52 to display a warning when the power source is running low. Alternatively or additionally, the power-supply manager may manage the recharging of power source 26 by a wireless charger. Alternatively or additionally, the detector may comprise a file manager, configured to manage the saving of information to, and retrieval of information from, memory 46. Alternatively or additionally, the detector may comprise a data exchange manager, configured to manage the exchange of data with an external device. The detector may further comprise a transceiver, such as a Bluetooth transceiver, configured to perform such an exchange of data.

In some embodiments, processor 42 is implemented solely in hardware, e.g., using one or more Application-Specific Integrated Circuits (ASICs) or Field-Programmable Gate Arrays (FPGAs). In other embodiments, the processor is at least partly implemented in software. For example, in some embodiments, the processor is embodied as a programmed digital computing device comprising at least a central processing unit (CPU) and random access memory (RAM). Program code, including software programs, and/or data, are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Optical Detector

Like piezoelectric detector 22a, optical detector 22b comprises membrane 32, and typically further comprises display 52, along with PCB 40 and at least some of the above-described components that are mounted on PCB 40, such as processor 42. Optical detector 22b differs from piezoelectric detector 22a, however, in that optical detector 22b does not use a piezoelectric microphone to convert deflections of the membrane into electric signals. Rather, the optical detector uses an optical system to perform this conversion, as described in detail below.

In the optical detector, membrane 32—and in particular, at least part of inner face 36 of membrane 32—is optically reflective. For example, membrane 32 may be made of an optically reflective material, or inner face 36 may be at least partly coated with a reflective coating 60, comprising, for example, silver. The optical detector further comprises a light source 56, such as a laser diode, and an array 64 of photodetectors 66 (such as an array of photodiodes), each of which is disposed within the housing. For example, as shown in FIG. 1, light source 56 and photodetector array 64 may be mounted to the inside of the housing, on the upper surface of lower compartment 28a. Light source 56 transmits a light beam 62 onto the membrane, such that light beam 62 is reflected by the membrane, by virtue of reflective coating 60, onto array 64. As further described below, the location at which the reflected beam of light hits the photodetector array varies, as a function of the deflection of the membrane. Hence, by identifying the location at which the beam of light was reflected onto the array of photodetectors, the processor may ascertain the manner in which the membrane was deflected, and hence, may output a sound signal that represents the impinging sound waves.

Figure 3:
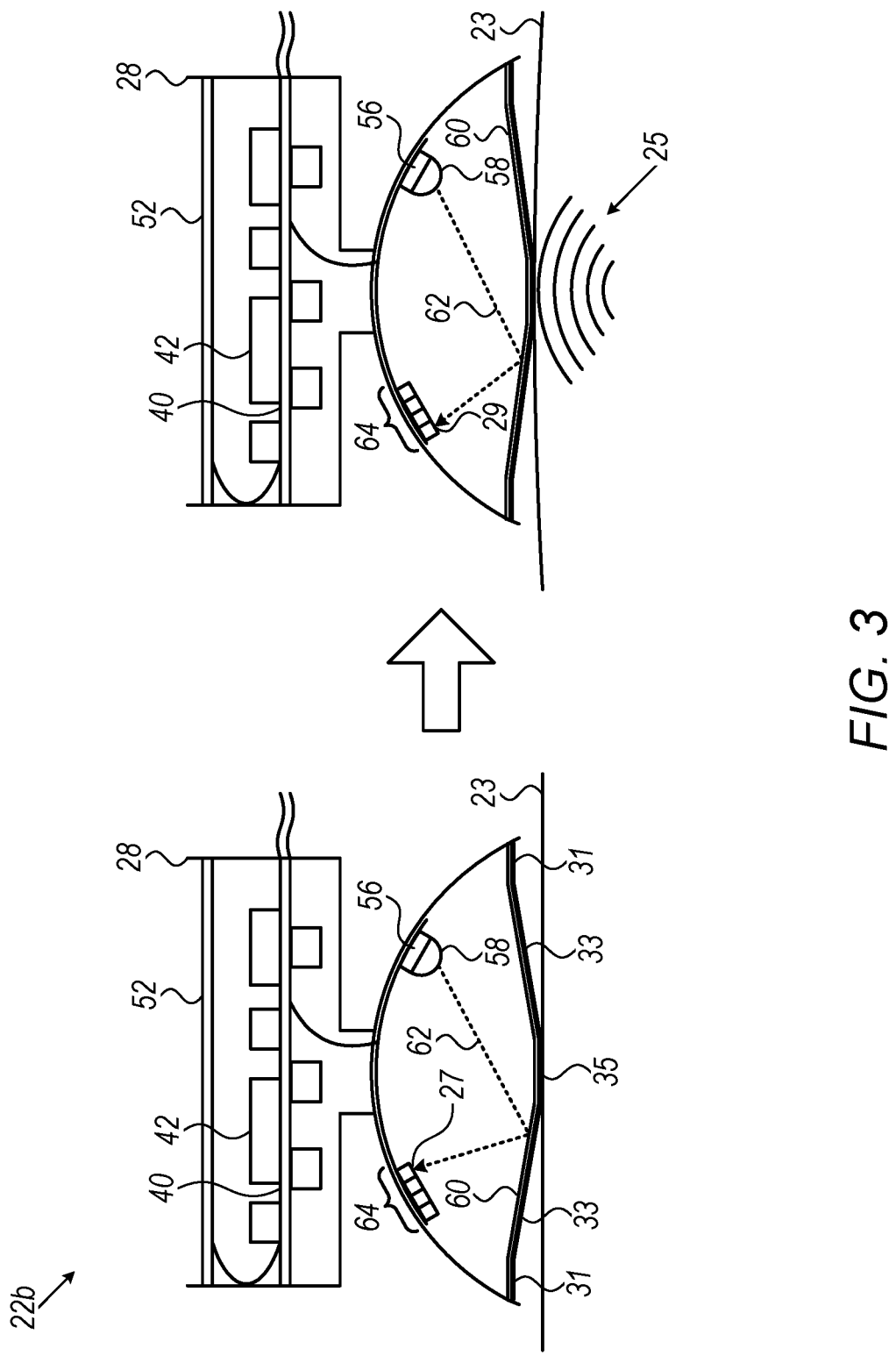

To further illustrate this concept, reference is now additionally made to FIGS. 2-3, which are schematic illustrations of the manner in which optical detector 22b operates, in accordance with some embodiments of the present invention. FIG. 3 is generally similar to FIG. 2, except for the alternative membrane shape shown in FIG. 3. In particular, whereas FIG. 2 shows a convex membrane, FIG. 3 shows a membrane that comprises a horizontal perimeter portion 31 mounted to the inside of the housing, a horizontal central portion 35 at the center of the membrane, and a slanted portion 33 that joins perimeter portion 31 to central portion 35. It is hypothesized by the inventors that this alternative shape may provide a higher-amplitude response to the impinging sound waves, such that the signal-to-noise ratio of the optical system is improved. (As noted earlier, however, any suitable membrane shape is included within the scope of the present disclosure.)

The left half of both FIG. 2 and FIG. 3 shows the optical detector held against the body 23 of a subject, such as against the subject's chest, such that membrane 32 contacts the body. Initially, in the absence of sound emanating from the body, light beam 62, upon being reflected by the membrane, strikes a first location 27 on the array of photodetectors. In contrast, upon sound waves 25 impinging on the membrane, as shown in the right half of both FIG. 2 and FIG. 3, the membrane is deflected inward, such that the reflected light beam strikes a second location 29 on the array of photodetectors. Likewise, as sound waves 25 continue to impinge on the membrane, the location at which reflected light beam strikes the array of photodetectors continues to vary, such that, as further described below with respect to FIG. 4, the processor may reconstruct the impinging sound waves responsively to this variation.

As described above in the Overview, the deflection of the membrane is generally small, such that the location at which the reflected light beam hits the photodetector array, referred to below as the "location of incidence," varies by only a small amount. Hence, the array of photodetectors typically consists of fewer than 10 photodetectors, such as between four and six photodetectors. An advantage of such a small number of photodetectors is that the processor may poll each of the photodetectors more frequently, such that the sound signal output by the processor has a higher sample rate. Alternatively or additionally, to facilitate a high sample rate, the processor may continuously poll the photodetectors. For example, the processor may run a dedicated execution thread that continuously iterates over the photodetectors, and obtains the outputs therefrom. Alternatively or additionally, to increase the sample rate, the processor may poll only those photodetectors that are near the previous location of incidence. (Array 64 may comprise a suitable control mechanism that facilitates this.) Such selective readout may be particularly helpful for embodiments in which larger arrays of photodetectors—such as arrays having tens or hundreds of photodetectors—are used.

In some embodiments, optical detector 22b further comprises a cylindrical lens 58, configured to focus the beam of light into a line, such that the line is reflected onto the array of photodetectors. In other words, cylindrical lens 58 causes the beam of light to be reflected as a line, rather than as a point, onto the array of photodetectors. This renders the optical detector more robust, in that the array of photodetectors may detect the reflected beam of light, even if the position of the array, or the light source, varies slightly over the lifetime of the optical detector.

Although not shown in the figures, the optical detector typically further comprises accelerometer 48. The accelerometer may be coupled to housing 28 in any suitable fashion, such that the accelerometer detects chest movements of the subject when the detector contacts the subject's chest. For example, the accelerometer may be coupled to the housing by being coupled to the inner face of the membrane, as in the piezoelectric detector. Alternatively, the accelerometer may be coupled to any suitable location on the outside or inside surface of housing 28.

Figure 4A:
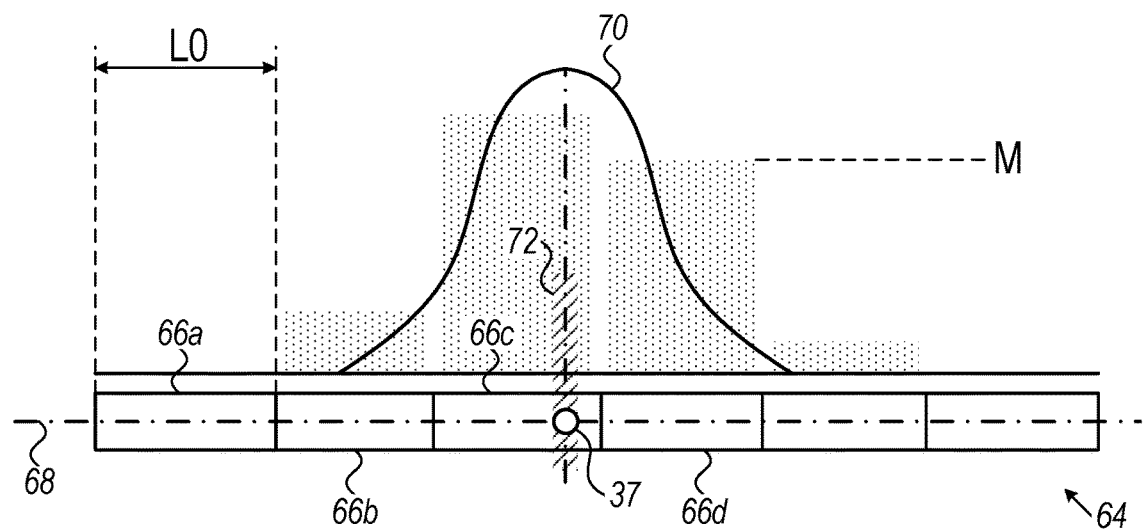
FIGS. 4A-B show a method for identifying the location at which a reflected beam of light hits a photodetector array, and constructing a sound signal in response thereto, in accordance with some embodiments of the present invention.
Figure 4B:
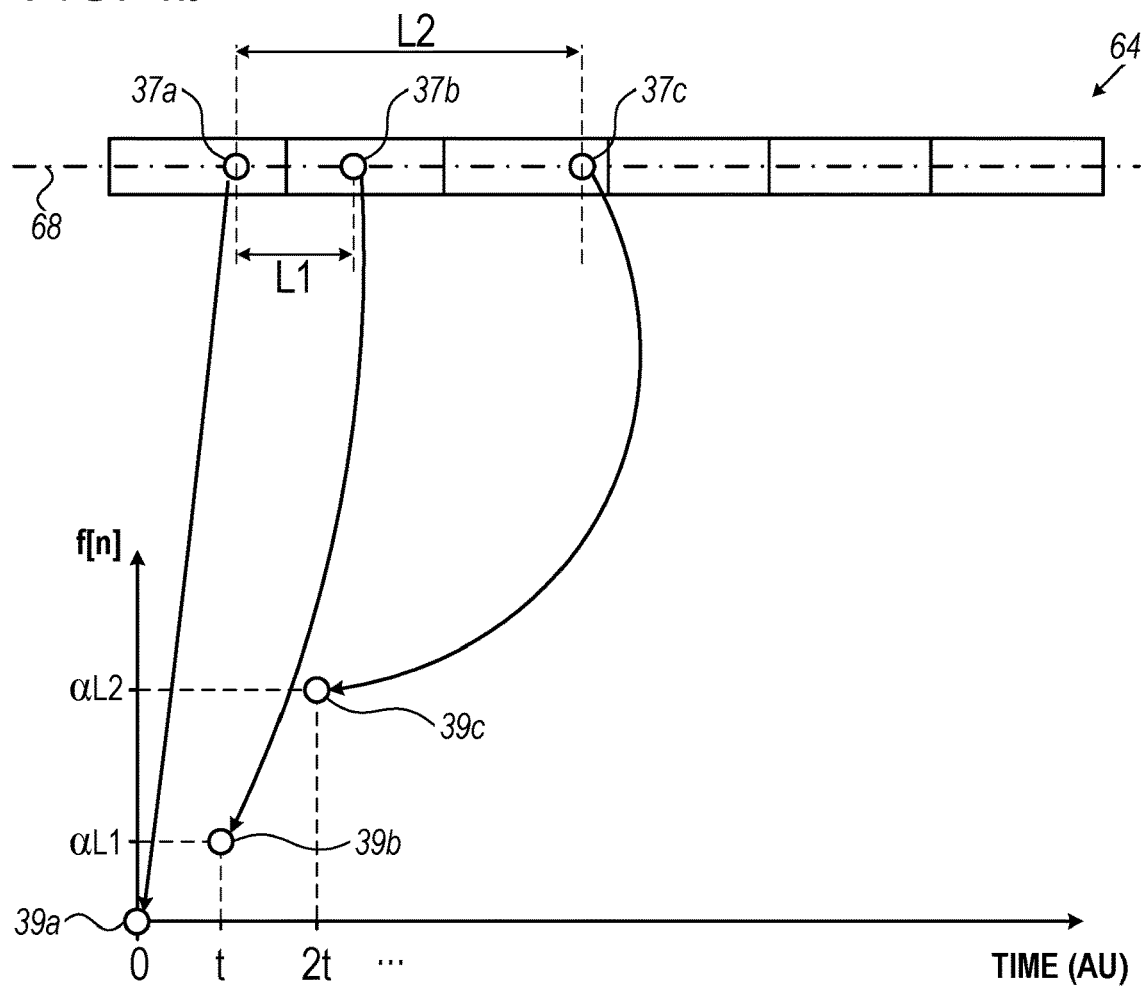

Reference is now made to FIGS. 4A-B, which show a method for identifying the location at which a reflected beam of light hits photodetector array 64, and for constructing a sound signal f[n] in response thereto, in accordance with some embodiments of the present invention.

FIGS. 4A-B show the face of array 64 that faces the membrane, and hence, is struck by the reflected light beam 72. (This face of the array is perpendicular to the face of the array that is shown in FIGS. 1-3.) In the particular example shown in FIGS. 4A-B, array 64 comprises six photodetectors, four of which are explicitly identified in FIG. 4A as a first photodetector 66a, a second photodetector 66b, a third photodetector 66c, and a fourth photodetector 66d. Each of the photodetectors in array 64 has a length L0 that is parallel to the longitudinal axis 68 of array 64.

As described above, reflected light beam 72 may strike the array at a point, or, as illustrated in FIG. 4A, as a line that is approximately perpendicular to longitudinal axis 68, further to the focusing of the light beam by cylindrical lens 58. In either case, the processor may identify the location 37 along longitudinal axis 68 at which the reflected light beam strikes the array, referred to below as the "location of incidence," by analyzing the voltage or current signals output by the photodetectors.

(As implied immediately below, the photons in the light beam are typically not confined to a sharply defined line or point, but rather, are spread in a Gaussian distribution. For ease of description however, the present specification, including the claims, may refer to the light beam having the shape of a line or point, if the center of the light beam—i.e., the region of the light beam having the greatest photon density—is in the shape of a line or point. Similarly, for ease of illustration, FIG. 4A shows the center of the light beam—referred to above as the "reflected light beam 72"—striking third photodetector 66c, without showing the full spread of incident photons across the array. Similarly, references herein, including in the claims, to "the location at which the reflected light beam strikes the array" refer to the location at which the center of the reflected light beam strikes the array.)

To identify the location of incidence, the processor may first receive, from each of the photodetectors, a signal having a magnitude M that indicates the amount of light (i.e., the number of photons), from the reflected beam of light, detected by the photodetector. (For example, magnitude M may be proportional to the amount of light striking the photodetector.) The processor may then identify location of incidence 37 as the location of the photodetector that detected the greatest amount of reflected light. In the case of FIG. 4A, this photodetector is third photodetector 66c.

In some embodiments, the processor ascertains the location of incidence more precisely, with a resolution that is less than length L0 of each of the photodetectors. To do this, the processor fits the respective signal magnitudes M to a Gaussian distribution 70, and then identifies the location of incidence as the center of Gaussian distribution 70. For example, as illustrated in FIG. 4A, the processor may pinpoint the location of incidence on third photodetector 66c, near the edge of third photodetector 66c that borders fourth photodetector 66d, based on the center of the Gaussian distribution being at this location.

FIG. 4B shows the construction of sound signal f[n], based on the identification of a first location of incidence 37a, a second location of incidence 37b, and a third location of incidence 37c. First location of incidence 37a is assumed to correspond to location 27 in FIGS. 2-3, i.e., the "default location" of the incident reflection when the membrane is in its rest state, not subject to any time-varying external forces.

First, at time 0, the processor identifies first location of incidence 37a, and adds a first point 39a to the signal responsively thereto. Since location of incidence 37a is the default location of incidence, first point 39a has a magnitude of zero. Next, at a time t, the processor identifies second location of incidence 37b, and adds a second point 39b to the signal responsively thereto. Since the second location of incidence is at a distance L1 from the first location of incidence, the magnitude of second point 39b is αL1 greater than the magnitude of first point 39a, where a is a scalar value that scales distance along longitudinal axis 68 to sound-signal magnitude. Next, at a time 2t, the processor identifies third location of incidence 37c, and adds a third point 39c to the signal responsively thereto. Since the third location of incidence is at a distance L2 from the first location of incidence, the magnitude of third point 39c is αL2 greater than the magnitude of first point 39a.

In this manner, the processor may continue to poll the array at any suitable polling interval of t, successively adding samples to f[n] responsively to the identified locations of incidence. Typically, as described above, polling interval t is relatively short, i.e., the polling frequency (or "readout frequency") of the processor is relatively high. For example, the polling frequency may be at least 1000 Hz, i.e., the processor may poll each photodetector at least 1000 times per second.

Frequency Stretching

As noted above, the membrane deflects in response to both sonic and infrasonic sound waves, such that the sound signal output by the processor has both sonic components, representing the sonic sound waves, and infrasonic components, represent the infrasonic sound waves. Equivalently, it may be said that the sound waves that impinge on the membrane have both sonic and infrasonic components, which are represented by, respectively, the sonic and infrasonic components of the sound signal that is output by the processor.

Advantageously, embodiments of the present invention facilitate playing the sound signal, such that even the infrasonic components of the signal are audible to the physician. For example, the processor may perform a technique referred to herein as "frequency stretching," which, given a "stretch factor" R>1, causes each component of the signal that is initially at a frequency f to be translated to a frequency R*f. In this manner, the infrasonic components of the sound signal are moved to a range of audible frequencies (e.g., 500 Hz-4 kHz), yet the harmonic relationships of the signal are preserved. In contrast, an alternative process of "frequency shifting," which, given a shift $f_s$, causes each component of the signal that is initially at a frequency f to be shifted to $f+f_s$, does not preserve the harmonic relationships of the signal.

For example, using frequency stretching with a factor of 2.5, a signal having a fundamental frequency $f_0$ of 1 kHz and harmonic frequencies of 2 kHz ($=2f_0$) and 5 kHz ($=5f_0$) may be altered such that (i) the infrasonic components of the signal are moved to the audible range, and (ii) the signal has a new fundamental frequency $f_1$ of 2.5 kHz, with new harmonic frequencies of 5 kHz ($=2f_1$) and 12.5 kHz ($=5f_1$). (In other words, the ratios of the harmonic frequencies to the fundamental frequency are preserved.) In contrast, using frequency shifting to shift the signal by 1.5 kHz would result in the same fundamental frequency $f_1$ of 2.5 kHz ($=f_0+1.5$ kHz), but harmonic frequencies of 3.5 kHz ($=2$ kHz+1.5 kHz$\neq 2f_1$) and 6.5 kHz ($=5$ kHz+1.5 kHz$\neq 5f_1$).

Figure 5:
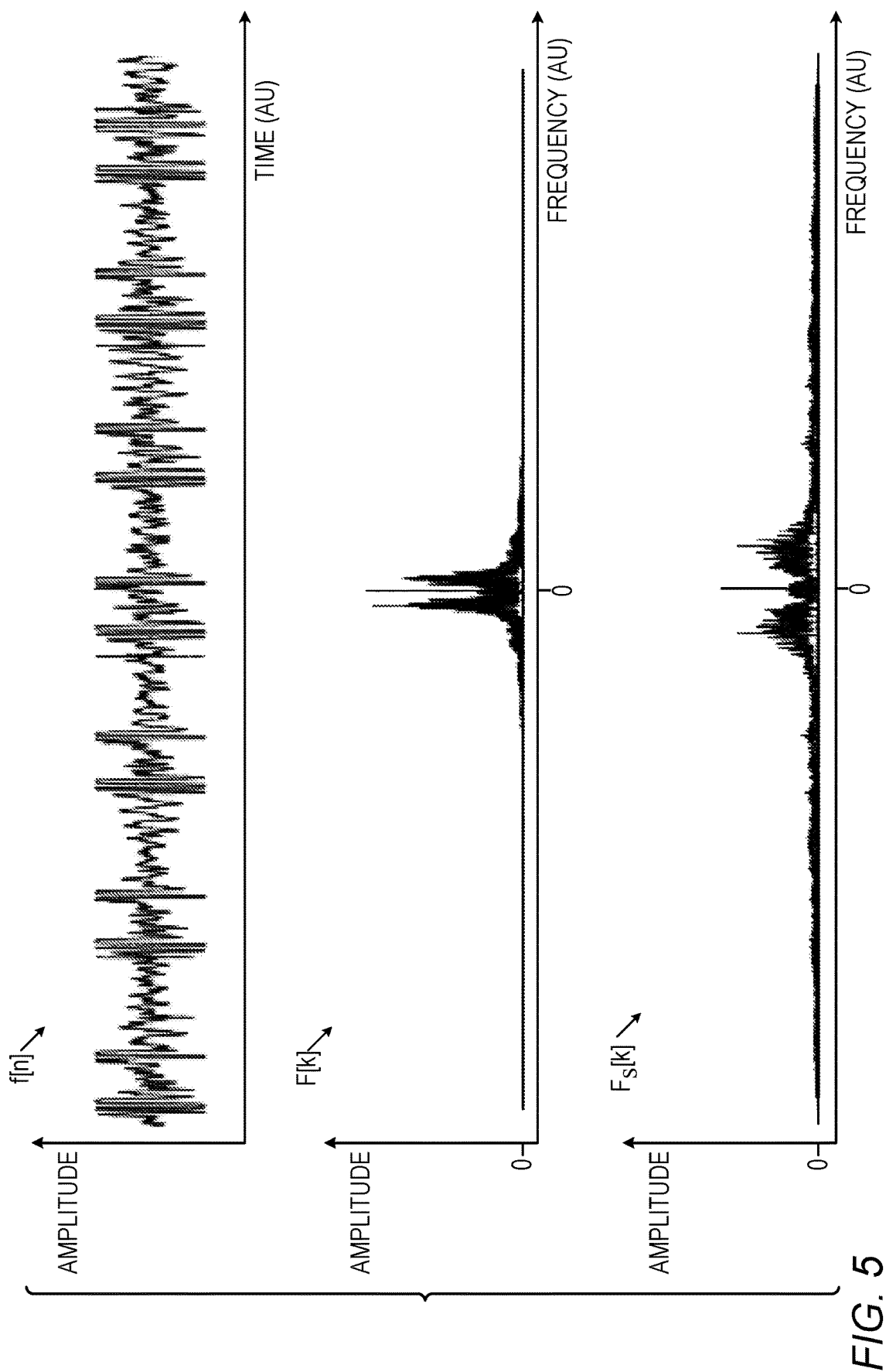
FIG. 5 is a schematic illustration of a frequency stretching of a signal, in accordance with some embodiments of the present invention.

In this regard, reference is now made to FIG. 5, which is a schematic illustration of a frequency stretching of a signal, in accordance with some embodiments of the present invention.

FIG. 5 shows, in the time domain, a discrete sound signal f[n], computed by processor 42 in response to output from the piezoelectric microphone or photodetector array, as described above. FIG. 5 further shows F[k], the fast Fourier transform (FFT) of f[n]. As can be seen, the main components of F[k] are near the zero frequency, such that most of the signal is infrasonic.

To translate these infrasonic components to a range of audible frequencies, the processor first computes F(m, k), the short-time Fourier transform (STFT) of f[n], by applying the formula $F(m, k)=\Sigma_n f[n]*w[n-m]*e^{-jkn}$, where m and k are both discrete variables (m being the time variable and k being the frequency variable), and w[n] is a suitable window function, such as a Hamming, Gaussian, or Hanning window function. Next, the processor decimates F(m, k) in the time domain—i.e., in the time variable m—by a factor R, where R is any rational number, such as to yield a decimated STFT $F_d(m, k)$. For example, if F(m, k) is of size 100×100, and R=5, then $F_d(m, k)$ will be of size 20×100. Next, the processor computes $f_d[n]$, the inverse STFT of $F_d(m, k)$, by applying the formula $f_d[n]=1/2\pi\Sigma_m\Sigma_k F_d(m, k)*e^{jkn}$. Finally, the processor interpolates $f_d[n]$ by the factor R, such as to yield a frequency-stretched signal $f_s[n]$ that has the same number of samples as the original f[n], but is stretched to higher frequencies. FIG. 5 shows $F_s[k]$, the FFT of $f_s[n]$. As can be observed, $F_s[k]$ appears stretched, relative to F[k], in that the components of F[k] that were near zero have been spread over a higher range of frequencies.

The factor R is typically chosen such that the lowest infrasonic component of the signal is moved to the desired audible frequency range, while the highest sonic component of the signal remains audible (i.e., does not become ultrasonic). For example, it will be assumed that the lowest infrasonic component of the signal is at 10 Hz, and the highest sonic component is at 150 Hz, i.e., the FFT of f[n] does not show any components lower than 10 Hz, or higher than 150 Hz, having at least a certain minimum amplitude. In such a case, assuming the desired audible frequency range begins at 500 Hz, the processor may choose R=50 (=500/10), since this factor will move the component at 10 Hz to 500 Hz, without causing the highest component (which is moved to 50*150 Hz=7.5 kHz) to become inaudible.

Auscultation and Imaging System

Figure 6:
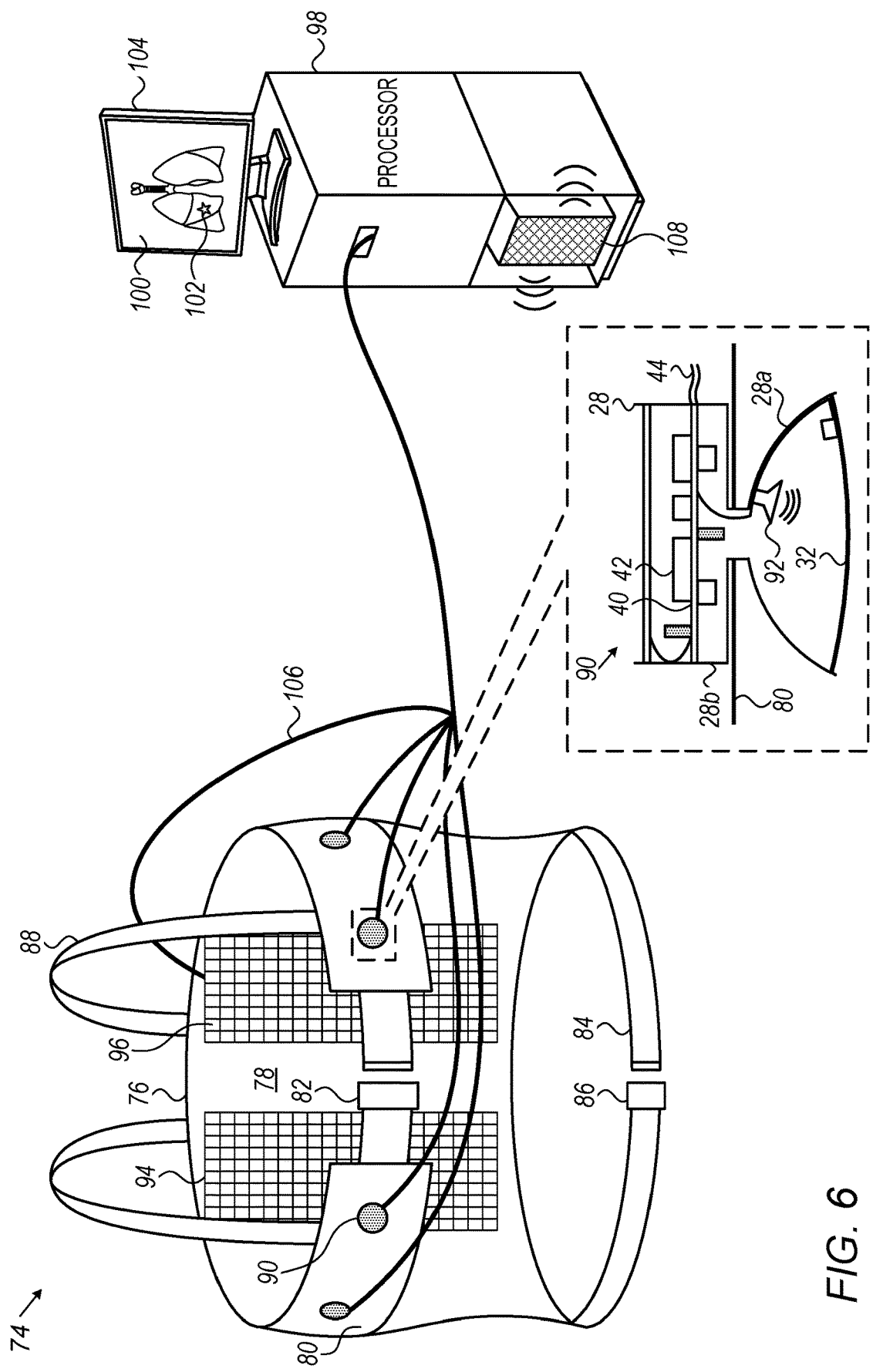
FIG. 6 is a schematic illustration of an auscultation and imaging system, in accordance with some embodiments of the present invention.

Reference is now made to FIG. 6, which is a schematic illustration of an auscultation and imaging system 74, in accordance with some embodiments of the present invention.

System 74 comprises a garment 76, such as a vest, a belt, a cloak, a sweater, a band, an apron, or any other garment configured to cover at least a portion of the body of a subject. For example, the particular embodiment of garment 76 shown in FIG. 6 comprises a "backward apron," comprising a back portion 78, configured to cover the back of a subject, one or more, e.g., two, bands 80 extending from opposite sides of back portion 78, configured to couple to one another over the chest of the subject such that the bands cover the chest of the subject, and two shoulder straps 88 running between the back portion and bands 80, configured to pass over the shoulders the subject. As shown, an adjustable buckle 82 may couple bands 80 to one another, such that, by adjusting buckle 82 (i.e., by using the buckle to move the two bands closer together or farther apart), the garment may be made to conform to the size and shape of the subject. To further facilitate a good fit, two straps 84 may extend from opposite sides of the back portion, at or near the bottom of the garment, and may similarly be coupled to one another via a second adjustable buckle 86. Alternatively or additionally, shoulder straps 88 may be adjustable.

System 74 further comprises one or more sound transmitters 92 coupled to the garment. For example, a plurality of sound detection-and-transmission units 90, each of which includes a sound transmitter 92 (e.g., a piezoelectric sound transmitter), may be coupled to the garment, e.g., by being coupled to bands 80. As described below, sound transmitters 92 are configured to transmit sound through the body of the subject, at least for the purpose of imaging the subject (e.g., imaging lungs of the subject), and/or for ascertaining the volume of air within the subject's lungs.

Aside from the inclusion of sound transmitters 92, detection-and-transmission units 90 may be similar or identical to the sound detectors described above with reference to FIG. 1. For example, each sound detection-and-transmission unit 90 may comprise a piezoelectric or optical sound detector that includes, within housing 28, the relevant sound-detection components described above, along with a sound transmitter 92. In such embodiments, as shown in FIG. 6, sound transmitter 92 is typically coupled to the upper surface of lower compartment 28a, and is wiredly connected to PCB 40. Each detection-and-transmission unit may be coupled to the garment such that upper compartment 28b of the unit is on the outside of the garment, and lower compartment 28a of the unit is on the inside of the garment, such that membrane 32 contacts the body of the subject.

System 74 further comprises a plurality of sound detectors coupled to the garment. These sound detectors are configured to detect two types of sound, namely, (i) the sound transmitted by sound transmitters 92, following passage of the transmitted sound through the body of the subject, and (ii) body sound emanating from the body of the subject. In some embodiments, each of the sound detectors is configured to detect both of these types of sound. In other embodiments, some of the sound detectors are configured to detect mainly the transmitted sound, by virtue of being configured to detect the range of frequencies of the transmitted sound, while others of the sound detectors are configured to detect mainly the body sound, by virtue of being configured to detect the (lower) range of body-sound frequencies, including, for example, infrasonic frequencies. For example, FIG. 6 shows an embodiment in which a plurality of transmitted-sound detectors 96 detect mainly the transmitted sound, while the optical or piezoelectric detectors in sound detection-and-transmission units 90 detect mainly body sound, as described above with reference to FIGS. 1-3.

Typically, transmitted-sound detectors 96 are positioned opposite sound transmitters 92. For example, transmitted-sound detectors 96 may be arranged in one or more (e.g., two) two-dimensional arrays 94 coupled to back portion 78, such that the transmitted-sound detectors are opposite the sound transmitters, which are coupled to bands 80, when the garment is worn by the subject.

System 74 further comprises a processor 98, configured to process the outputs generated by the sound detectors responsively to detecting the transmitted sound and the body sound, and to generate an output in response thereto. For example, as further described below, processor 98 may construct, by processing the sound-detector outputs, an image 100 of the interior of the body of the subject, such as an image of the subject's lungs. The processor may then output this image, by displaying the image on a display 104. The processor may also locate, by processing the sound-detector outputs, the source of a body sound, and may further indicate the location of the source in the image, e.g., by displaying a suitable marker 102 over the portion of image 100 that corresponds to the location of the source. The processor may also control the sound transmitters, and/or any other components of system 74 coupled to garment 76.

In some embodiments, processor 98 performs all of the body-sound detection functions described above with reference to FIGS. 1-4, in addition to the processing, output, and control functions described with reference to FIG. 6 and subsequent figures. In such embodiments, sound detection-and-transmission units 90 need not necessarily comprise "local" processors 42. In other embodiments, local processors 42 perform the sound detection functions described above with reference to FIGS. 1-4, while processor 98 acts as a "global" processor, processing information from all of the local processors, and from transmitted-sound detectors 96. For example, each of the local processors may, by performing the body-sound detection techniques described above, generate a respective body-sound signal. The body-sound signals may then be passed to processor 98, which may then process these signals, along with the signals from transmitted-sound detectors 96, and generate an output in response to the processing. For example, as described above, processor 98 may construct, and then display, an image in which the location of the body-sound source is marked. Alternatively or additionally, the processor may combine the multiple body-sound signals into a combined body-sound signal, and then play this combined signal via a speaker 108.

In some embodiments, before playing body sounds that include infrasonic components, processor 98 applies frequency stretching as described above with reference to FIG. 5, in order to translate the infrasonic components to an audible range of frequencies. In some embodiments, system 74 comprises two or more speakers 108, and/or two earphones (as in FIG. 1). In such embodiments, the processor may stereophonically play the body-sound signal to the user, through the two or more channels provided by the speakers or earphones, in accordance with the location of the sound source that was identified by the processor.

In some embodiments, processor 98 is configured to analyze the signals received from the sound detectors, such as to automatically diagnose a particular ailment from which the subject suffers, or otherwise identify the subject's condition, based on characteristics of these signals.

Typically, system 74 further comprises an input device. For example, display 104 may comprise a touch screen, and/or system 74 may additionally comprise a keyboard and/or a mouse. Using such an input device, a physician may cause system 74 to perform any suitable function that is within the scope of the present disclosure.

In some embodiments, as shown in FIG. 6, the various components coupled to garment 76 are wiredly connected to processor 98, via a plurality of cables 106. In other embodiments, the components are wirelessly connected to the processor. In some embodiments, system 74 further comprises a spirometer (not shown), which is also connected to processor 98, e.g., via a universal serial bus (USB) connection. In such embodiments, processor 98 may display, next to image 100, any lung-capacity measurements acquired by the spirometer, and/or may use such measurements to better assess the subject's status.

In general, system 74 may be used in any suitable setting. For example, primary care physicians may use the system to confirm or rule out certain lung or heart conditions. Alternatively, hospitals may use the system for early detection, for tracking the subject's condition, and/or for facilitating treatment. As an example of treatment facilitation, the system may be used to monitor the response of the subject's lungs to any medicines the subject is taking, or to monitor and control mechanical ventilation of the subject. Alternatively, system 74 may be used for assessing the expected effect of a lung resection.

Processor 98 may be embodied as a single processor, or as a cooperatively networked or clustered set of processors. Processor 98 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Locating Sound Sources

One advantage of the multiple body-sound detectors of system 74 is that the location of body-sound sources may be identified. In this regard, reference is now made to FIG. 7, which is a schematic illustration of a technique for identifying the location of a body-sound source, in accordance with some embodiments of the present invention.

In some embodiments, processor 98 identifies the location of the source of a body sound by applying a three-dimensional model 110, of at least a portion of the subject's body, that indicates, for each cell 112 in the model, the time required for a sound wave emanating from the cell to reach each one of the sound detectors, when the subject is wearing the garment. In particular, using such a model, the processor may locate the source of a particular body sound (at the resolution of a single cell), based on the delays between the body-sound detectors in detecting the body sound.

Figure 7:
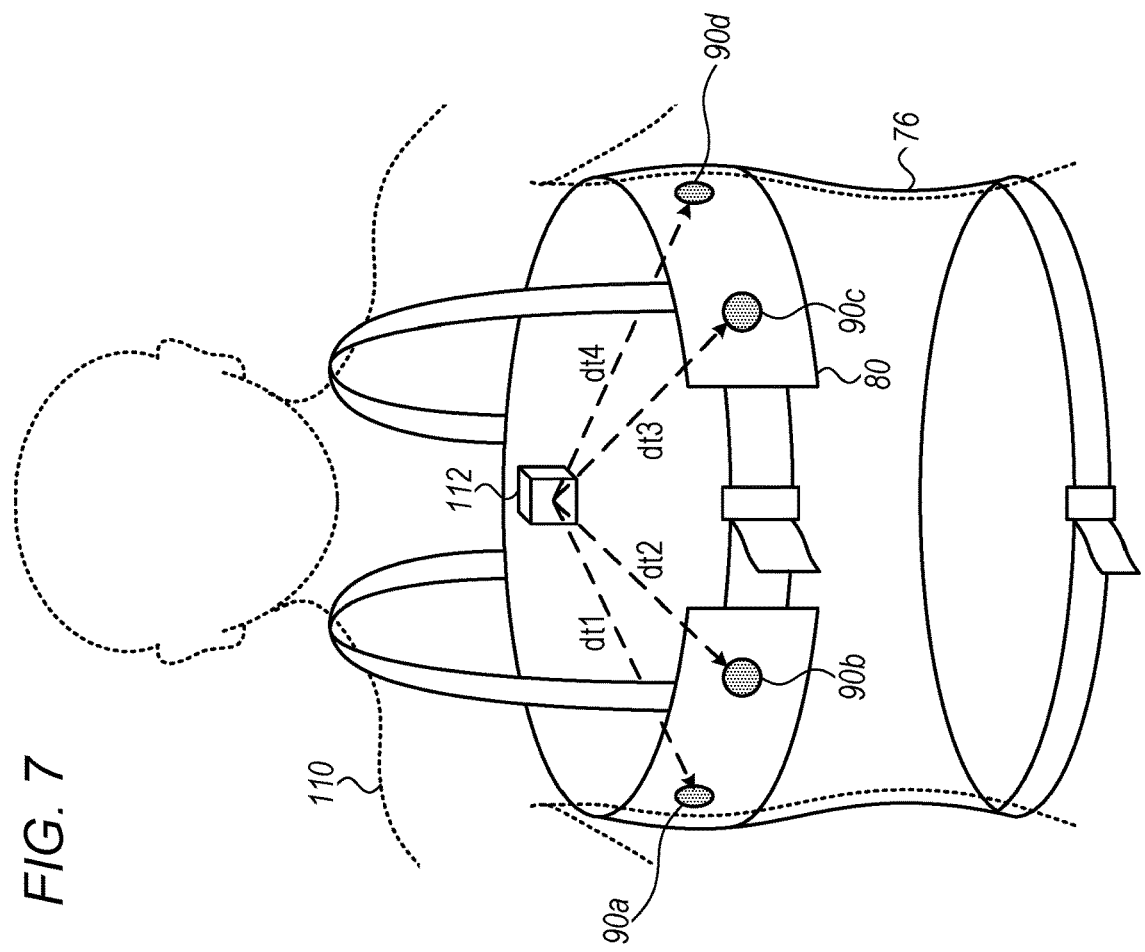
FIG. 7 is a schematic illustration of a technique for identifying the location of a body-sound source, in accordance with some embodiments of the present invention.

For example, for the particular cell 112 shown in FIG. 7, model 110 indicates that a sound wave emanating from the cell reaches a first sound detection-and-transmission unit 90*a* after a time of dt1 seconds, a second sound detection-and-transmission unit 90*b* after a time of dt2 seconds, a third sound detection-and-transmission unit 90*c* after a time of dt3 seconds, and a fourth sound detection-and-transmission unit 90*d* after a time of dt4 seconds. Thus, for example, assuming dt1 is less than dt2, dt3, and dt4, if a particular sound was detected at a time of zero seconds by first sound detection-and-transmission unit 90*a*, at approximately dt2−dt1 seconds by second sound detection-and-transmission unit 90*b*, at approximately dt3−dt1 seconds by third sound detection-and-transmission unit 90*c*, and at approximately dt4−dt1 seconds by fourth sound detection-and-transmission unit 90*d*, the processor may ascertain that the sound emanated from the portion of the subject's body corresponding to cell 112.

Alternatively or additionally, the processor may locate the source of a body sound by identifying the angle of the source of the body sound with respect to each of a plurality of lines of sound detectors. In this regard, reference is now made to FIG. 8, which is a schematic illustration of a multilinear arrangement of sound detectors, in accordance with some embodiments of the present invention.

Figure 8:
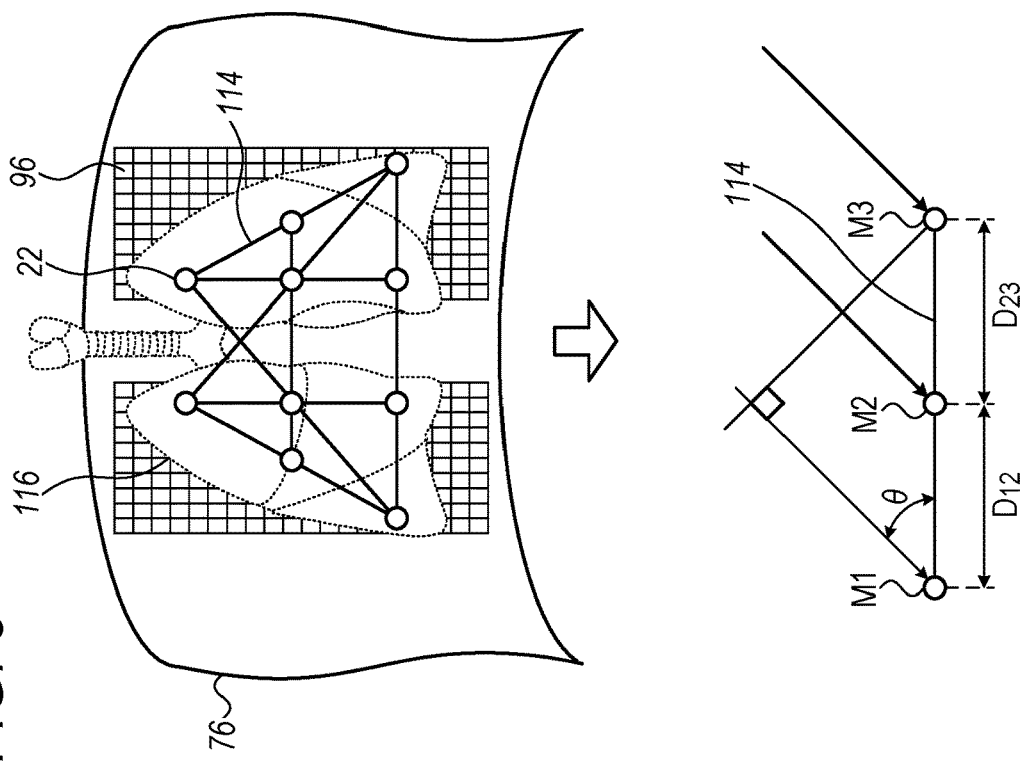
FIG. 8 is a schematic illustration of a multilinear arrangement of sound detectors, in accordance with some embodiments of the present invention.

In the embodiment of FIG. 8, a plurality of body-sound detectors 22 are coupled to the back portion of garment 76, alternatively or additionally to the body-sound detectors coupled to bands 80. (For clarity, bands 80 are not shown in FIG. 8.) As shown, these body-sound detectors may be interspersed among transmitted-sound detectors 96. To facilitate identifying the location of body-sound sources, the body-sound detectors are arranged in a plurality of lines 114. To facilitate locating lung-sound sources, the detectors may be positioned on the garment such that, when the garment is worn by the subject, the detectors cover a large portion of the subject's lungs 116, as illustrated in FIG. 8.

To locate a sound source using the configuration of FIG. 8, the processor first identifies the angle of the source with respect to each of lines 114. To do this, the processor sweeps through a plurality of angles. For each of these angles, the processor, for each of the detectors in the line, delays the output of the detector in accordance with the angle and with the position of the detector on the line, and then sums the delayed outputs, such as to yield a summed output. The processor then identifies the angle of the source of the body sound as the angle for which the power of the summed output is highest, relative to the other angles.

By way of illustration, the bottom of FIG. 8 shows a line of three sound detectors, comprising a first detector M1, a second detector M2 located at a distance $D_{12}$ from first detector M1, and a third detector M3 located at a distance $D_{23}$ from second detector M2. It will be assumed that each of these detectors detected a sound, and generated an output in response thereto. In particular, it will be assumed that first detector M1 generated a first output $x1(t)$, second detector M2 generated a second output $x2(t)$, and third detector M3 generated a third output $x3(t)$. To identify the angle of the sound source with respect to this line of detectors, the processor may sweep through several angles θ, e.g., from 0 to 180 degrees in increments of 5 degrees. For each angle θ, second detector M2 is expected to detect the sound wave $D_{23}*\cos(\theta)/S$ seconds after third detector M3, where S is an estimated speed of sound in the body. Similarly, first detector M1 is expected to detect the sound wave $(D_{23}+D_{12})*\cos(\theta)/S$ seconds after third detector M3. (For θ greater than 90 degrees, these quantities are negative, indicating that the sound is first detected by first detector M1.) Hence, the processor may delay $x2(t)$ by $del_{23}(\theta)=D_{23}*\cos(\theta)/S$ seconds, and $x1(t)$ by $del_{13}(\theta)=(D_{23}+D_{12})*\cos(\theta)/S$ seconds. The sum $Z(\theta, t)$ of the delayed outputs is thus $x3(t)+x2(t-del_{23}(\theta))+x1(t-del_{13}(\theta))$, and the power of $Z(\theta, t)$, assuming $Z(\theta, t)$ is a discrete signal, is $P(\theta)=\Sigma_t Z(\theta, t)^2$. Assuming that $P(\theta)$ reaches a maximum at $\theta=\theta_{max}$, the processor may identify $\theta_{max}$ as the angle of the sound source with respect to the line of detectors.

After identifying the angle of the sound source with respect to each line 114, the processor may then identify the point at which the sound source is located. Typically, this requires that the sound detectors comprise at least three pairwise non-parallel lines, each having three or more sound detectors. (A set of lines is said to be "pairwise non-parallel" if no two lines from the set are parallel with one another.) For example, after performing the above technique for three lines, the processor may have three angles of maximum power: $\theta_{max}$, $\phi_{max}$, and $\varphi_{max}$. Each of these angles implies a respective plane on which the sound source is assumed to lie. By intersecting these three planes, the processor may find the point at which the sound source is located. (Even if fewer than three lines of sound detectors are available, the processor may nevertheless calculate the plane or line on which the sound source is located, and present this information to the physician.)

Advantageously, as illustrated in FIG. 8, the body-sound detectors may be arranged such that each of at least some of the sound detectors belongs to at least three lines 114 of three or more detectors. Such an arrangement facilitates a relatively large number of lines, using a relatively small number of detectors. (In general, as the number of lines increases beyond three, so does the accuracy with which the sound source is located, even if some of the lines are parallel with each other.)

It is noted that the location-identification techniques described herein with reference to FIGS. 7-8 may be practiced with any suitable alternative embodiment of garment 76, and even without any garment at all. For example, for certain alternative embodiments of garment 76, such as where garment 76 comprises an apron having a front portion that covers the chest of the subject, detectors 22 may be coupled, in a multilinear arrangement, to the front of garment 76. Alternatively, garment 76 may comprise a meshwork of straps, and detectors 22 may be coupled to the junctions at which the straps meet. Alternatively, detectors 22 may be coupled directly to the subject's skin, e.g., using adhesive patches.

Imaging and Air Volume Estimation

Figure 9:
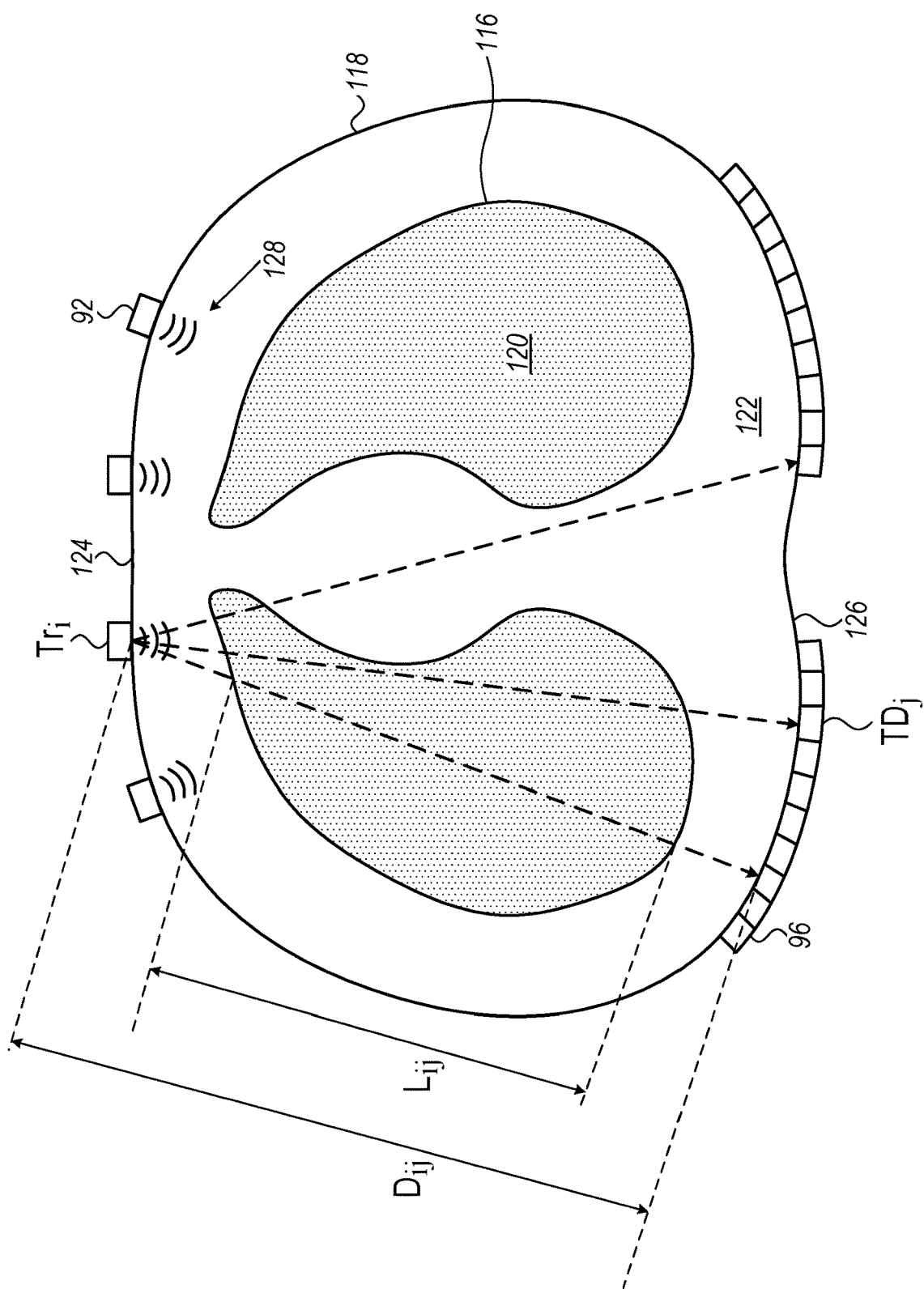
FIG. 9 is a schematic illustration of a technique for imaging and air volume estimation, in accordance with some embodiments of the present invention.

Reference is now made to FIG. 9, which is a schematic illustration of a technique for imaging and air volume estimation, in accordance with some embodiments of the present invention. (Although FIG. 9 pertains mainly to imaging of the lungs, it is noted that the imaging techniques described herein may be used to acquire images of any suitable interior portion of a subject's body.)

FIG. 9 shows a schematic cross section through the upper torso 118 of a subject, assuming that the subject is wearing the embodiment of garment 76 shown in FIGS. 6-7, such that sound transmitters 92 (or the sound detection-and-transmission units in which these transmitters are contained) are in contact with the chest 124 of the subject, and transmitted-sound detectors 96 are in contact with the back 126 of the subject. The cross section of FIG. 9 cuts through lungs 116 of the subject, such that two types of media lie between the sound transmitters and the transmitted-sound detectors: tissue 122, assumed to comprise mostly water, and the air 120 that is present in the lungs.

To acquire a three-dimensional image of lungs 116, processor 98 (FIG. 6) causes each transmitter 92 to transmit a sound signal 128 through the lungs. As sound signal 128 passes through tissue 122 and air 120, the signal is attenuated. Hence, based on the intensity with which the signal is detected by each of the transmitted-sound detectors, the processor may construct an image of the lungs, using computed tomography (CT) techniques. Subsequently, as described above with reference to FIG. 6, the processor may display the image on display 104.

It is noted that the imaging techniques described herein differ from regular ultrasound imaging, in that the frequencies of sound signals 128 are less than those used in ultrasound imaging. For example, sound signals 128 may be transmitted at between 25 kHz and 200 kHz, which is only slightly above the sonic (audible) range of frequencies. Alternatively, sound signals 128 may be transmitted in the sonic range of frequencies, such as at frequencies between 500 Hz and 10 kHz. In general, an advantage of transmitting at lower frequencies, relative to regular ultrasound imaging, is that the sound signals are able to pass through the air in the lungs. (In contrast to computed tomography and radiography, the imaging techniques used in system 74 produce little, if any, harmful radiation.)

In some embodiments, to facilitate differentiating sound signal 128 from background noise and body sounds, each sound signal 128 is a chirp signal—i.e., a signal of time-varying frequency. Typically, each sound transmitter transmits a sound signal that is orthogonal to each of the sound signals transmitted by the other transmitters; in other words, each of the transmitters uses a different range of frequencies. Hence, all of the transmitters may transmit at the same time, since the processor may, by filtering the signal that is output by each detector 96, differentiate between each of the transmitted signals.

Alternatively or additionally to acquiring an image of the lungs, the processor may estimate the volume of air 120 within the lungs, responsively to the respective delays with which the transmitted sound is detected by the sound detectors. For example, based on the delay $T_{ij}$ for a sound signal transmitted by a transmitter $Tr_i$ and detected by a transmitted-sound detector $TD_j$, the processor may estimate the path length $L_{ij}$ that is travelled, through the lungs, by the signal, for i=1 . . . N, N being the number of transmitters 92, and j=1 . . . M, M being the number of transmitted-sound detectors 96. The processor may then estimate the volume of air in the lungs by summing the path lengths $\{L_{ij}\}$, and then multiplying this sum by a suitable signal cross-sectional area. (To reduce or eliminate any coinciding or crossing-over of paths, which would lead to "double counting" in the summation of path lengths, each transmitter may be configured to transmit at a sufficiently narrow angle, such as an angle that is less than 20 degrees.) Typically, the processor then correlates this estimate with the stage of the subject's respiratory cycle, which, as described above with reference to FIG. 1, may be identified based on output from accelerometers 48. The processor may further display a curve, which tracks the estimated volume of air in the subject's lungs over the subject's respiratory cycle.

To estimate the path length $L_{ij}$, the processor first calculates the delay $T_{ij}$, which is the duration from transmission of the signal from transmitter $Tr_i$ to detection of the signal by detector $TD_j$. Next, given a distance $D_{ij}$ between transmitter $Tr_i$ and detector $TD_j$, the processor calculates the path length $L_{ij}$, by applying the equation $L_{ij}=(T_{ij}*S_{tissue}-D_{ij})*S_{air}/(S_{tissue}-S_{air})$, where $S_{tissue}$ is the speed of sound in tissue 122 (which is typically assumed to be the same as the speed of sound in water), and $S_{air}$ is the speed of sound in air.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for detecting sound waves emanating from a body of a subject, the apparatus comprising:
   a housing;
   a membrane, disposed at an opening of the housing, configured to deflect, when an outer face of the membrane contacts the body, responsively to the sound waves impinging on the membrane;
   a piezoelectric microphone, disposed within the housing, configured to detect vibrations of air caused by the deflection of the membrane, and to generate a microphone output in response thereto;
   an accelerometer, disposed on an inner face of the membrane, configured to deflect, along with the membrane, at frequencies below a minimum frequency that is detectable by the piezoelectric microphone, and to generate an accelerometer output in response thereto; and
   a processor, configured to process the microphone output and the accelerometer output, and to generate, responsively to the processing, a sound signal that represents the impinging sound waves.

2. The apparatus according to claim 1, wherein the membrane comprises a material having a specific acoustic impedance that is between 0.8 and 4.5 MPa·s/m.

3. The apparatus according to claim 2, wherein the material is selected from the group consisting of: polyethylene, polyamide, and polymethyl methacrylate.

4. The apparatus according to claim 1, further comprising a second microphone, disposed within the housing, configured to detect ambient noise that does not emanate from the body of the subject, and to generate a noise-detection output in response thereto,
   wherein the processor is configured to generate the sound signal by adaptively filtering the microphone output, based on the noise-detection output.

5. The apparatus according to claim 4, further comprising a printed circuit board (PCB) disposed within the housing, wherein the piezoelectric microphone is mounted on a face of the PCB that faces the membrane, and the second microphone is mounted on an opposite face of the PCB, facing away from the membrane.

6. The apparatus according to claim 1, further comprising a printed circuit board (PCB) disposed within the housing, wherein the processor and the microphone are mounted on the PCB.

7. The apparatus according to claim 1, further comprising a display coupled to the housing such that the display faces away from the membrane, wherein the processor is further configured:
   to analyze the sound signal, and
   to drive the display to display results of the analysis.

8. The apparatus according to claim 1, further comprising earphones connected to the housing, wherein the processor is further configured to play the sound signal through the earphones.

9. The apparatus according to claim 8, wherein the processor is configured to play infrasonic components of the sound signal, which represent infrasonic components of the sound waves, by translating the infrasonic components of the sound signal to a range of audible frequencies.

10. The apparatus according to claim 9, wherein the processor is configured to translate the infrasonic components to the range of audible frequencies by:
    computing a short-time Fourier transform (STFT) of the sound signal,
    decimating the STFT of the sound signal, in a time domain of the STFT of the sound signal, by a factor R,
    computing an inverse STFT of the decimated STFT of the sound signal, and
    interpolating the inverse STFT by the factor R.

11. The apparatus according to claim 9, wherein the range of audible frequencies is between 500 Hz and 4 kHz.

12. The apparatus according to claim 1, further comprising a sound transmitter disposed within the housing, configured to transmit sound through the body of the subject.

13. The apparatus according to claim 12, wherein the sound transmitter is configured to transmit the sound at a frequency between 25 kHz and 200 kHz.

14. The apparatus according to claim 12, wherein the sound transmitter is configured to transmit the sound at a frequency between 500 Hz and 10 kHz.

15. The apparatus according to claim 12, wherein the sound transmitter is configured to transmit the sound by transmitting a chirp signal.

16. A method for detecting sound waves emanating from a body of a subject, the method comprising:
    by contacting the body of the subject with an outer face of a membrane that is disposed at an opening of a housing, causing the membrane to deflect responsively to the sound waves impinging on the membrane;
    using a piezoelectric microphone disposed within the housing, detecting vibrations of air caused by the deflection of the membrane, and generating a microphone output in response thereto;
    using an accelerometer that is disposed on an inner face of the membrane, detecting the deflection of the membrane at frequencies below a minimum frequency that is detectable by the piezoelectric microphone, and generating an accelerometer output in response thereto; and using a processor, processing the microphone output and the accelerometer output, and generating, responsively to the processing, a sound signal that represents the impinging sound waves.

17. The method according to claim 16, wherein the sound waves emanate from lungs of the subject.

18. The method according to claim 16, further comprising, using the processor, playing the sound signal through earphones connected to the housing.

19. The method according to claim 18, wherein playing the sound signal comprises playing infrasonic components of the sound signal, which represent infrasonic components of the sound waves, by translating the infrasonic components of the sound signal to a range of audible frequencies.

20. The method according to claim 19, wherein translating the infrasonic components to the range of audible frequencies comprises:
   computing a short-time Fourier transform (STFT) of the sound signal,
   decimating the STFT of the sound signal, in a time domain of the STFT of the sound signal, by a factor R,
   computing an inverse STFT of the decimated STFT of the sound signal, and
   interpolating the inverse STFT by the factor R.

21. The method according to claim 19, wherein the range of audible frequencies is between 500 Hz and 4 kHz.

* * * * *